(12) United States Patent
Gera et al.

(10) Patent No.: US 12,186,028 B2
(45) Date of Patent: *Jan. 7, 2025

(54) ROTATING MARKER FOR IMAGE GUIDED SURGERY

(71) Applicant: AUGMEDICS LTD., Yokneam (IL)

(72) Inventors: Tomer Gera, Kfar Tavor (IL); Nissan Elimelech, Beerotaim (IL); Nitzan Krasney, Haifa (IL); Stuart Wolf, Yokneam (IL)

(73) Assignee: AUGMEDICS LTD., Yokneam (IL)

( * ) Notice: Subject to any disclaimer, the term of this patent is extended or adjusted under 35 U.S.C. 154(b) by 183 days.

This patent is subject to a terminal disclaimer.

(21) Appl. No.: 18/008,980

(22) PCT Filed: Jun. 15, 2021

(86) PCT No.: PCT/IB2021/055242
§ 371 (c)(1),
(2) Date: Dec. 8, 2022

(87) PCT Pub. No.: WO2021/255627
PCT Pub. Date: Dec. 23, 2021

(65) Prior Publication Data
US 2023/0329799 A1 Oct. 19, 2023

Related U.S. Application Data

(63) Continuation-in-part of application No. 16/901,026, filed on Jun. 15, 2020, now Pat. No. 11,389,252.

(51) Int. Cl.
*A61B 34/20* (2016.01)
*A61B 34/10* (2016.01)
(Continued)

(52) U.S. Cl.
CPC ............. *A61B 34/20* (2016.02); *A61B 34/10* (2016.02); *A61B 90/39* (2016.02); *G06T 19/003* (2013.01);
(Continued)

(58) Field of Classification Search
CPC ......... A61B 34/20; A61B 34/10; A61B 90/39; A61B 2034/107; A61B 2034/2055;
(Continued)

(56) References Cited

U.S. PATENT DOCUMENTS 3,690,776 A 9/1972 Zaporoshan
4,459,358 A 7/1984 Berke
(Continued)

FOREIGN PATENT DOCUMENTS

CA 3022448 A1 2/2018
CA 3034314 A1 2/2018
(Continued)

OTHER PUBLICATIONS

US 11,395,705 B2, 09/2022, Lang (withdrawn)
(Continued)

*Primary Examiner* — Maurice L. McDowell, Jr.
(74) *Attorney, Agent, or Firm* — KNOBBE, MARTENS, OLSON & BEAR, LLP

(57) ABSTRACT

A marker (40) for image guided surgery, consisting of a base (94), having a base axis, connecting to a clamp (42), and an alignment target (44). The alignment target includes a target region (120) having an alignment pattern formed thereon, and a socket (124) connected to the target region and configured to fit rotatably to the base, whereby the alignment target is rotatable about the base axis. The alignment target also includes an optical indicator (162) for the socket indicating an angle of orientation of the alignment target about the base axis.

22 Claims, 13 Drawing Sheets

(51) Int. Cl.
*A61B 90/00* (2016.01)
*G06T 19/00* (2011.01)

(52) U.S. Cl.
CPC ...... *G06T 19/006* (2013.01); *A61B 2034/107* (2016.02); *A61B 2034/2055* (2016.02); *A61B 2090/3904* (2016.02); *G06T 2210/41* (2013.01)

(58) Field of Classification Search
CPC .. A61B 2090/3904; A61B 2017/00477; A61B 2090/365; A61B 2090/371; A61B 2090/372; A61B 2090/3916; A61B 2090/3983; A61B 2090/3991; A61B 90/36; A61B 2090/502; G06T 19/003; G06T 19/006; G06T 2210/41
See application file for complete search history.

(56) References Cited

U.S. PATENT DOCUMENTS

| | | | |
|---|---|---|---|
| 4,711,512 | A | 12/1987 | Upatnieks |
| 4,863,238 | A | 9/1989 | Brewster |
| 4,944,739 | A | 7/1990 | Torre |
| 5,100,420 | A | 3/1992 | Green et al. |
| 5,357,292 | A | 10/1994 | Wiedner |
| 5,410,802 | A | 5/1995 | Buckley |
| 5,441,042 | A | 8/1995 | Putman |
| 5,442,146 | A | 8/1995 | Bell et al. |
| 5,510,832 | A | 4/1996 | Garcia |
| D370,309 | S | 5/1996 | Stucky |
| 5,620,188 | A | 4/1997 | McCurry et al. |
| 5,636,255 | A | 6/1997 | Ellis |
| 5,665,092 | A | 9/1997 | Mangiardi et al. |
| 5,743,731 | A | 4/1998 | Lares et al. |
| 5,771,121 | A | 6/1998 | Hentschke |
| 5,792,046 | A | 8/1998 | Dobrovolny |
| 5,841,507 | A | 11/1998 | Barnes |
| 6,006,126 | A | 12/1999 | Cosman |
| 6,038,467 | A | 3/2000 | De Bliek et al. |
| 6,125,164 | A | 9/2000 | Murphy et al. |
| 6,138,530 | A | 10/2000 | McClure |
| 6,147,805 | A | 11/2000 | Fergason |
| 6,227,667 | B1 | 5/2001 | Halldorsson et al. |
| 6,256,529 | B1 | 7/2001 | Holupka et al. |
| 6,285,505 | B1 | 9/2001 | Melville et al. |
| 6,314,310 | B1 | 11/2001 | Ben-Haim et al. |
| 6,349,001 | B1 | 2/2002 | Spitzer |
| 6,444,192 | B1 | 9/2002 | Mattrey |
| 6,447,503 | B1 | 9/2002 | Wynne et al. |
| 6,449,090 | B1 | 9/2002 | Omar et al. |
| 6,456,405 | B2 | 9/2002 | Horikoshi et al. |
| 6,456,868 | B2 | 9/2002 | Saito et al. |
| 6,474,159 | B1 | 11/2002 | Foxlin et al. |
| 6,518,939 | B1 | 2/2003 | Kikuchi |
| 6,527,777 | B2 | 3/2003 | Justin |
| 6,529,331 | B2 | 3/2003 | Massof et al. |
| 6,549,645 | B1 | 4/2003 | Oikawa et al. |
| 6,578,962 | B1 | 6/2003 | Amir et al. |
| 6,609,022 | B2 | 8/2003 | Vilsmeier et al. |
| 6,610,009 | B2 | 8/2003 | Person |
| D480,476 | S | 10/2003 | Martinson et al. |
| 6,659,611 | B2 | 12/2003 | Amir et al. |
| 6,675,040 | B1 | 1/2004 | Cosman |
| 6,683,584 | B2 | 1/2004 | Ronzani et al. |
| 6,690,964 | B2 | 2/2004 | Bieger et al. |
| 6,714,810 | B2 | 3/2004 | Grzeszczuk et al. |
| 6,737,425 | B1 | 5/2004 | Yamamoto et al. |
| 6,740,882 | B2 | 5/2004 | Weinberg |
| 6,757,068 | B2 | 6/2004 | Foxlin |
| 6,759,200 | B1 | 7/2004 | Stanton, Jr. |
| 6,847,336 | B1 | 1/2005 | Lemelson et al. |
| 6,856,324 | B2 | 2/2005 | Sauer et al. |
| 6,856,826 | B2 | 2/2005 | Seeley et al. |
| 6,891,518 | B2 | 5/2005 | Sauer et al. |
| 6,900,777 | B1 | 5/2005 | Hebert et al. |
| 6,919,867 | B2 | 7/2005 | Sauer |
| 6,921,167 | B2 | 7/2005 | Nagata |
| 6,966,668 | B2 | 11/2005 | Cugini et al. |
| 6,980,849 | B2 | 12/2005 | Sasso |
| 6,993,374 | B2 | 1/2006 | Sasso |
| 6,997,552 | B1 | 2/2006 | Hung |
| 6,999,239 | B1 | 2/2006 | Martins et al. |
| 7,000,262 | B2 | 2/2006 | Bielefeld |
| 7,035,371 | B2 | 4/2006 | Boese et al. |
| 7,043,961 | B2 | 5/2006 | Pandey et al. |
| 7,072,435 | B2 | 7/2006 | Metz et al. |
| 7,103,233 | B2 | 9/2006 | Stearns |
| 7,107,091 | B2 | 9/2006 | Jutras et al. |
| 7,112,656 | B2 | 9/2006 | Desnoyers et al. |
| 7,141,812 | B2 | 11/2006 | Appleby et al. |
| 7,157,459 | B2 | 1/2007 | Ohta et al. |
| 7,169,785 | B2 | 1/2007 | Timmer et al. |
| 7,171,255 | B2 | 1/2007 | Holupka et al. |
| 7,176,936 | B2 | 2/2007 | Sauer et al. |
| 7,187,792 | B2 | 3/2007 | Fu et al. |
| 7,190,331 | B2 | 3/2007 | Genc et al. |
| 7,194,295 | B2 | 3/2007 | Vilsmeier |
| 7,215,322 | B2 | 5/2007 | Genc et al. |
| 7,229,078 | B2 | 6/2007 | Lechot |
| 7,231,076 | B2 | 6/2007 | Fu et al. |
| 7,235,076 | B2 | 6/2007 | Pacheco |
| 7,239,330 | B2 | 7/2007 | Sauer et al. |
| 7,259,266 | B2 | 8/2007 | Carter et al. |
| 7,260,426 | B2 | 8/2007 | Schweikard et al. |
| 7,269,192 | B2 | 9/2007 | Hayashi |
| 7,281,826 | B2 | 10/2007 | Huang |
| 7,315,636 | B2 | 1/2008 | Kuduvalli |
| 7,320,556 | B2 | 1/2008 | Vagn-Erik |
| 7,330,578 | B2 | 2/2008 | Wang et al. |
| 7,359,535 | B2 | 4/2008 | Salla et al. |
| 7,364,314 | B2 | 4/2008 | Nilsen et al. |
| 7,366,934 | B1 | 4/2008 | Narayan et al. |
| 7,379,077 | B2 | 5/2008 | Bani-Hashemi et al. |
| 7,431,453 | B2 | 10/2008 | Hogan |
| 7,435,219 | B2 | 10/2008 | Kim |
| 7,450,743 | B2 | 11/2008 | Sundar et al. |
| 7,458,977 | B2 | 12/2008 | McGinley et al. |
| 7,462,852 | B2 | 12/2008 | Appleby et al. |
| 7,493,153 | B2 | 2/2009 | Ahmed et al. |
| 7,505,617 | B2 | 3/2009 | Fu et al. |
| 7,507,968 | B2 | 3/2009 | Wollenweber et al. |
| 7,518,136 | B2 | 4/2009 | Appleby et al. |
| 7,525,735 | B2 | 4/2009 | Sottilare et al. |
| D592,691 | S | 5/2009 | Chang |
| D592,692 | S | 5/2009 | Chang |
| D592,693 | S | 5/2009 | Chang |
| 7,536,216 | B2 | 5/2009 | Geiger et al. |
| 7,542,791 | B2 | 6/2009 | Mire et al. |
| 7,556,428 | B2 | 7/2009 | Sukovic et al. |
| 7,557,824 | B2 | 7/2009 | Holliman |
| 7,563,228 | B2 | 7/2009 | Ma et al. |
| 7,567,834 | B2 | 7/2009 | Clayton et al. |
| 7,570,791 | B2 | 8/2009 | Frank et al. |
| 7,586,686 | B1 | 9/2009 | Hall |
| D602,620 | S | 10/2009 | Cristoforo |
| 7,605,826 | B2 | 10/2009 | Sauer |
| 7,606,613 | B2 | 10/2009 | Simon et al. |
| 7,607,775 | B2 | 10/2009 | Hermanson et al. |
| 7,620,223 | B2 | 11/2009 | Xu et al. |
| 7,623,902 | B2 | 11/2009 | Pacheco |
| 7,627,085 | B2 | 12/2009 | Boyden et al. |
| 7,630,753 | B2 | 12/2009 | Simon et al. |
| 7,633,501 | B2 | 12/2009 | Wood et al. |
| 7,645,050 | B2 | 1/2010 | Wilt et al. |
| 7,653,226 | B2 | 1/2010 | Guhring et al. |
| 7,657,075 | B2 | 2/2010 | Viswanathan |
| 7,689,019 | B2 | 3/2010 | Boese et al. |
| 7,689,042 | B2 | 3/2010 | Brunner et al. |
| 7,689,320 | B2 | 3/2010 | Prisco et al. |
| 7,699,486 | B1 | 4/2010 | Beiner |
| 7,699,793 | B2 | 4/2010 | Goette et al. |
| 7,719,769 | B2 | 5/2010 | Sugihara et al. |
| D617,825 | S | 6/2010 | Chang |
| 7,734,327 | B2 | 6/2010 | Colquhoun |

(56) References Cited

U.S. PATENT DOCUMENTS

| | | |
|---|---|---|
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park et al. |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,965,583 B2 | 2/2015 | Ortmaier et al. |
| 8,969,829 B2 | 3/2015 | Wollenweber et al. |
| 8,989,349 B2 | 3/2015 | Thomson et al. |
| 8,992,580 B2 | 3/2015 | Bar et al. |
| 8,994,729 B2 | 3/2015 | Nakamura |

(56) References Cited

U.S. PATENT DOCUMENTS

| | | |
|---|---|---|
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |
| 9,085,643 B2 | 7/2015 | Svanborg et al. |
| 9,087,471 B2 | 7/2015 | Miao |
| 9,100,643 B2 | 8/2015 | McDowall et al. |
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Ponce |
| 9,286,730 B2 | 3/2016 | Bar-Zeev et al. |
| 9,289,267 B2 | 3/2016 | Sauer et al. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico |
| 9,387,008 B2 | 7/2016 | Sarvestani |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park |
| 9,443,488 B2 | 9/2016 | Borenstein |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Nanqing |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen |
| 9,561,446 B2 | 2/2017 | Brecher |
| 9,565,415 B2 | 2/2017 | Zhang et al. |
| 9,572,661 B2 | 2/2017 | Robin |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque |
| 9,684,980 B2 | 6/2017 | Royalty et al. |
| 9,690,119 B2 | 6/2017 | Garofolo et al. |
| RE46,463 E | 7/2017 | Feinbloom |
| 9,693,748 B2 | 7/2017 | Rai et al. |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,746,739 B2 | 8/2017 | Alton et al. |
| 9,757,034 B2 | 9/2017 | Desjardins |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,839,448 B2 | 12/2017 | Reckling et al. |
| 9,844,413 B2 | 12/2017 | Daon et al. |
| 9,851,080 B2 | 12/2017 | Wilt |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |

(56) References Cited

U.S. PATENT DOCUMENTS

| | | |
|---|---|---|
| 9,901,414 B2 | 2/2018 | Lively |
| 9,911,187 B2 | 3/2018 | Steinle |
| 9,911,236 B2 | 3/2018 | Bar et al. |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,042,167 B2 | 8/2018 | McDowall et al. |
| 10,046,165 B2 | 8/2018 | Frewin |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman |
| 10,207,315 B2 | 2/2019 | Appleby |
| 10,212,517 B1 | 2/2019 | Beltran et al. |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat |
| 10,433,814 B2 | 10/2019 | Razzaque |
| 10,434,335 B2 | 10/2019 | Takahashi |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,466,487 B2 | 11/2019 | Blum et al. |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,602,114 B2 | 2/2020 | Casas |
| 10,577,630 B2 | 3/2020 | Zhang |
| 10,586,400 B2 | 3/2020 | Douglas |
| 10,591,737 B2 | 3/2020 | Yildiz et al. |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |

(56) References Cited

U.S. PATENT DOCUMENTS

| | | |
|---|---|---|
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi |
| 10,626,473 B2 | 4/2020 | Mariani |
| 10,631,905 B2 | 4/2020 | Asfora et al. |
| 10,631,907 B2 | 4/2020 | Zucker |
| 10,634,331 B1 | 4/2020 | Feinbloom |
| 10,634,921 B2 | 4/2020 | Blum et al. |
| 10,638,080 B2 | 4/2020 | Ovchinnikov |
| 10,646,285 B2 | 5/2020 | Siemionow et al. |
| 10,650,513 B2 | 5/2020 | Penney et al. |
| 10,650,594 B2 | 5/2020 | Jones |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori |
| 10,706,540 B2 | 7/2020 | Merlet |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare |
| 10,748,319 B1 | 8/2020 | Tao et al. |
| 10,758,315 B2 | 9/2020 | Johnson et al. |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Leung et al. |
| 10,799,145 B2 | 10/2020 | Found |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone |
| 10,835,296 B2 | 11/2020 | Elimelech |
| 10,838,206 B2 | 11/2020 | Fortin-Deschenes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,869,727 B2 | 12/2020 | Yanof et al. |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas et al. |
| 10,893,260 B2 | 1/2021 | Trail et al. |
| 10,895,742 B2 | 1/2021 | Schneider |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit |
| 10,921,613 B2 | 2/2021 | Gupta et al. |
| 10,928,321 B2 | 2/2021 | Rawle |
| 10,928,638 B2 | 2/2021 | Ninan |
| 10,929,670 B1 | 2/2021 | Troy et al. |
| 10,935,815 B1 | 3/2021 | Castaneda |
| 10,935,816 B2 | 3/2021 | Ban et al. |
| 10,936,537 B2 | 3/2021 | Huston |
| 10,939,973 B2 | 3/2021 | Dimaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | McDowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,016,302 B2 | 5/2021 | Freeman et al. |
| 11,019,988 B2 | 6/2021 | Fiebel et al. |
| 11,027,027 B2 | 6/2021 | Manning et al. |
| 11,029,147 B2 | 6/2021 | Abovitz et al. |
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | Leboeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,187,907 B2 | 11/2021 | Osterman et al. |
| 11,202,682 B2 | 12/2021 | Staunton et al. |
| 11,207,150 B2 | 12/2021 | Healy et al. |
| 11,217,028 B2 | 1/2022 | Jones et al. |

(56) References Cited

U.S. PATENT DOCUMENTS

| | | | |
|---|---|---|---|
| 11,224,483 B2 | 1/2022 | Steinberg et al. |
| 11,224,763 B2 | 1/2022 | Takahashi et al. |
| 11,227,417 B2 | 1/2022 | Berlinger et al. |
| 11,231,787 B2 | 1/2022 | Isaacs et al. |
| 11,243,404 B2 | 2/2022 | McDowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao et al. |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,373,342 B2 | 6/2022 | Stafford et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 * | 7/2022 | Gera ............... G06T 19/006 |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus et al. |
| 11,461,936 B2 | 10/2022 | Freeman et al. |
| 11,461,983 B2 | 10/2022 | Jones et al. |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Quiles Casas |
| 11,488,021 B2 | 11/2022 | Sun et al. |
| 11,490,986 B2 | 11/2022 | BEn-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | McGinley et al. |
| 2004/0171930 A1 | 9/2004 | Grimm et al. |
| 2004/0238732 A1 | 12/2004 | State et al. |
| 2005/0017972 A1 | 1/2005 | Poole et al. |
| 2005/0024586 A1 | 2/2005 | Teiwes et al. |
| 2005/0119639 A1 | 6/2005 | McCombs et al. |

(56) References Cited

U.S. PATENT DOCUMENTS

| | | |
|---|---|---|
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa et al. |
| 2006/0147100 A1* | 7/2006 | Fitzpatrick .............. G06T 7/344 382/154 |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0183041 A1 | 8/2007 | McCloy et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0036902 A1 | 2/2009 | DiMaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0238609 A1 | 9/2012 | Srivastava et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2013/0345718 A1 | 12/2013 | Crawford et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0230873 A1 | 8/2015 | Kubiak et al. |
| 2015/0230893 A1 | 8/2015 | Huwais |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |

(56) References Cited

U.S. PATENT DOCUMENTS

| | | |
|---|---|---|
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Gudicell et al. |
| 2016/0191887 A1 | 6/2016 | Casas |
| 2016/0223822 A1 | 8/2016 | Harrison et al. |
| 2016/0228033 A1 | 8/2016 | Rossner |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1 | 10/2016 | Gonzalez et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0164919 A1 | 6/2017 | Lavallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1 | 3/2018 | Srimohanarajah et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer et al. |
| 2018/0120106 A1 | 5/2018 | Sato |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0205606 A1 | 7/2019 | Zhou et al. |
| 2019/0216537 A1 | 7/2019 | Eltorai et al. |
| 2019/0251692 A1 | 8/2019 | Schmidt-Richberg et al. |
| 2019/0251694 A1 | 8/2019 | Han et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1 | 12/2019 | Wen et al. |
| 2019/0369717 A1 | 12/2019 | Frielinghaus et al. |
| 2019/0378276 A1 | 12/2019 | Flossmann et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |

(56) References Cited

U.S. PATENT DOCUMENTS

| | | |
|---|---|---|
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0375666 A1 | 12/2020 | Stephen |
| 2020/0377493 A1 | 12/2020 | Heiser et al. |
| 2020/0377956 A1 | 12/2020 | Vogelstein et al. |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zhang et al. |
| 2021/0225006 A1 | 7/2021 | Grady et al. |
| 2021/0227791 A1 | 7/2021 | De et al. |
| 2021/0231301 A1 | 7/2021 | Hikmet et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev et al. |
| 2021/0364802 A1 | 11/2021 | Uchiyama et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0382310 A1 | 12/2021 | Freeman et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0257206 A1 | 8/2022 | Hartley et al. |
| 2022/0269077 A1 | 8/2022 | Adema et al. |
| 2022/0270263 A1 | 8/2022 | Junio |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |

(56) References Cited

U.S. PATENT DOCUMENTS

| | | |
|---|---|---|
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Jiannyuh |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0386153 A1 | 11/2023 | Rybnikov et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Vilsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341861 A1 | 10/2024 | Wolf et al. |
| 2024/0341910 A1 | 10/2024 | Wolf et al. |
| 2024/0341911 A1 | 10/2024 | Elimelech et al. |

FOREIGN PATENT DOCUMENTS

| | | |
|---|---|---|
| CN | 101379412 A | 3/2009 |
| CN | 101379412 B | 3/2009 |
| CN | 103106348 A | 5/2013 |
| CN | 111915696 A | 11/2020 |
| CN | 112489047 A | 3/2021 |
| CN | 112489047 B | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2134847 A2 | 12/2009 |
| EP | 2557998 A1 | 2/2013 |
| EP | 2823463 A1 | 1/2015 |
| EP | 2868277 A1 | 5/2015 |
| EP | 2134847 B1 | 6/2015 |
| EP | 2891966 A1 | 7/2015 |
| EP | 2963616 A2 | 1/2016 |
| EP | 3028258 A1 | 6/2016 |
| EP | 3034607 A1 | 6/2016 |
| EP | 3037038 A1 | 6/2016 |
| EP | 3069318 A1 | 9/2016 |
| EP | 3076660 A1 | 10/2016 |
| EP | 2891966 B1 | 1/2017 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3256213 A1 | 12/2017 |
| EP | 3306567 A1 | 4/2018 |
| EP | 3320874 A1 | 5/2018 |
| EP | 2030193 B1 | 7/2018 |

(56) References Cited

FOREIGN PATENT DOCUMENTS

| | | |
|---|---|---|
| EP | 2225723 B1 | 2/2019 |
| EP | 2619622 B1 | 2/2019 |
| EP | 3034607 B1 | 3/2019 |
| EP | 2892558 B1 | 4/2019 |
| EP | 3494903 A1 | 6/2019 |
| EP | 2635299 B1 | 7/2019 |
| EP | 3505050 A1 | 7/2019 |
| EP | 3224376 B1 | 8/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 3711700 A1 | 9/2020 |
| EP | 2625845 B1 | 3/2021 |
| EP | 3789965 A1 | 3/2021 |
| EP | 3076660 B1 | 4/2021 |
| EP | 3858280 A1 | 8/2021 |
| EP | 3593227 B1 | 9/2021 |
| EP | 3913423 A1 | 11/2021 |
| EP | 3789965 B1 | 12/2021 |
| EP | 3634294 B1 | 1/2022 |
| EP | 3952331 A1 | 2/2022 |
| EP | 3960235 A1 | 3/2022 |
| EP | 3635683 B1 | 7/2022 |
| EP | 3602492 B1 | 11/2022 |
| EP | 4173590 A1 | 5/2023 |
| EP | 3533031 B1 | 8/2023 |
| EP | 4252695 A1 | 10/2023 |
| EP | 3195257 B1 | 11/2023 |
| EP | 3405909 B1 | 11/2023 |
| EP | 4270313 A1 | 11/2023 |
| EP | 4287120 A1 | 12/2023 |
| EP | 3488381 B1 | 2/2024 |
| EP | 3834768 B1 | 2/2024 |
| EP | 3903714 B1 | 2/2024 |
| EP | 4336450 A1 | 3/2024 |
| EP | 3814984 B1 | 4/2024 |
| EP | 4115389 B1 | 4/2024 |
| EP | 3752981 B1 | 5/2024 |
| EP | 4375948 A1 | 5/2024 |
| EP | 4383203 A1 | 6/2024 |
| GB | 2507314 A | 4/2014 |
| IL | 262864 A | 3/2019 |
| JP | 2004-237092 A | 8/2004 |
| JP | 2008-507361 A | 3/2008 |
| JP | 2009-514571 A | 4/2009 |
| JP | 2021-525186 A | 9/2021 |
| KR | 10-2014-0120155 A | 10/2014 |
| KR | 20140120155 A | 10/2014 |
| WO | 03/34705 A2 | 4/2003 |
| WO | 03034705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014167563 A1 | 10/2014 |
| WO | 2014174067 A1 | 10/2014 |
| WO | 2015058816 A1 | 4/2015 |
| WO | WO2015061752 A1 | 4/2015 |
| WO | WO2015109145 A1 | 7/2015 |
| WO | 2016151506 A1 | 9/2016 |
| WO | 2018/052966 A1 | 3/2018 |
| WO | 2018/073452 A1 | 4/2018 |
| WO | WO2018200767 A1 | 4/2018 |
| WO | 2018206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019195926 A1 | 10/2019 |
| WO | 2019211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |
| WO | 2021/188757 A1 | 9/2021 |
| WO | 2021/255627 A1 | 12/2021 |
| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023/003952 A1 | 1/2023 |
| WO | 2023281395 A1 | 1/2023 |
| WO | 2023/011924 A1 | 2/2023 |
| WO | 2023007418 A1 | 2/2023 |
| WO | 2023021448 A1 | 2/2023 |
| WO | 2023021450 A1 | 2/2023 |
| WO | 2023021451 A1 | 2/2023 |
| WO | 2023026229 A1 | 3/2023 |
| WO | 2023047355 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |
| WO | 2024/145341 A1 | 7/2024 |
| WO | 2024/160896 A1 | 8/2024 |
| WO | 2024/165508 A1 | 8/2024 |
| WO | 2024/173251 A1 | 8/2024 |
| WO | 2024/186811 A1 | 9/2024 |

OTHER PUBLICATIONS

Van Ooijen et al., "Noninvasive Coronary Imaging Using Electron Beam CT: Surface Rendering Versus vol. Rendering," Computers in Radiology, AJR, vol. 180, pp. 223-226, Jan. 2003.

(56) References Cited

OTHER PUBLICATIONS

Zhang et al., "Medical Volume Rendering Techniques," Independent Research, Spring 2014, arXiv:1802.07710v1, pp. 1-33, Feb. 21, 2018.
Romero, "Volume Ray Casting Techniques and Applications Using General Purpose Computations on Graphics Processing Units," Thesis/Dissertation Collections, Rochester Institute of Technology, RIT Scholar Works, pp. 1-140, Jun. 2009.
Liberadzki et al., "Structured-Light-Based System for Shape Measurement of the Human Body in Motion," Sensors, vol. 18, pp. 1-19, year 2018.
WEBSTER (ed.), "Structured Light Techniques and Applications," Wiley Encyclopedia of Electrical and Electronics Engineering, pp. 1-24, year 2016.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.
Lumus Ltd., "DK-32 See-through Wearable Display Development Kit", Rehovot, Israel, pp. 1-2, Dec. 24, 2013.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data , pp. 1-4, Feb. 2019.
Liu et al., "Marker orientation in fiducial registration", Medical Imaging 2003: Image Processing, Proceedings of SPIE vol. 5032, pp. 1176-1185, 2003.
Fingas, "Fraunhofer iPad app guides liver surgery through augmented reality", pp. 1-6, Aug. 22, 2013.
Sagitov et al., "Comparing Fiducial Marker Systems in the Presence of Occlusion", International Conference on Mechanical, System and Control Engineering (ICMSC), pp. 1-6, 2017.
International Application # PCT/IB2021/055242 Search Report dated Oct. 7, 2021.
Mitrasinovic et al., "Clinical and surgical applications of smart glasses", pp. 381-401, Technology and Health Care, issue 23, year 2015.
Martin-Gonzalez et al., "Head-mounted virtual loupe with sight-based activation for surgical applications", IEEE symposium on mixed and augmented reality, pp. 207-208, Oct. 19-22, 2009.
Figl et al., "A fully automated calibration method for an optical see-through head-mounted operating microscope with variable zoom and focus", pp. 1492-1499, IEEE transactions on medical imaging, vol. 24, No. 11, Nov. 2005.
Medithinq Co. Ltd., "Metascope: world's first wearable scope", pp. 1-7, Jan. 2023.
Martin-Gonzalez et al., "Sight-based magnification system for surgical applications", pp. 26-30, Conference proceedings of Bildverarbeitung für die Medizin, year 2010.
Burstrom et al., "Frameless patient tracking with adhesive optical skin markers for augmented reality surgical navigation in spine surgery", SPINE, vol. 45, No. 22, pp. 1598-1604, year 2020.
Suenaga et al., "Vision-based markerless registration using stereo vision and an augmented reality surgical navigation system: a pilot study", BMC Medical Imaging, pp. 1-11, year 2015.
Mayfield Clinic, "Spinal Fusion: Lateral Lumbar Interbody Fusion (LLIF)", pp. 1-6, Jan. 2021.
Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.
Kazanzides et al., "Systems and Methods for Augmented Reality Magnifying Loupe", case ID 15944, pp. 1-2, Nov. 26, 2020.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.

* cited by examiner

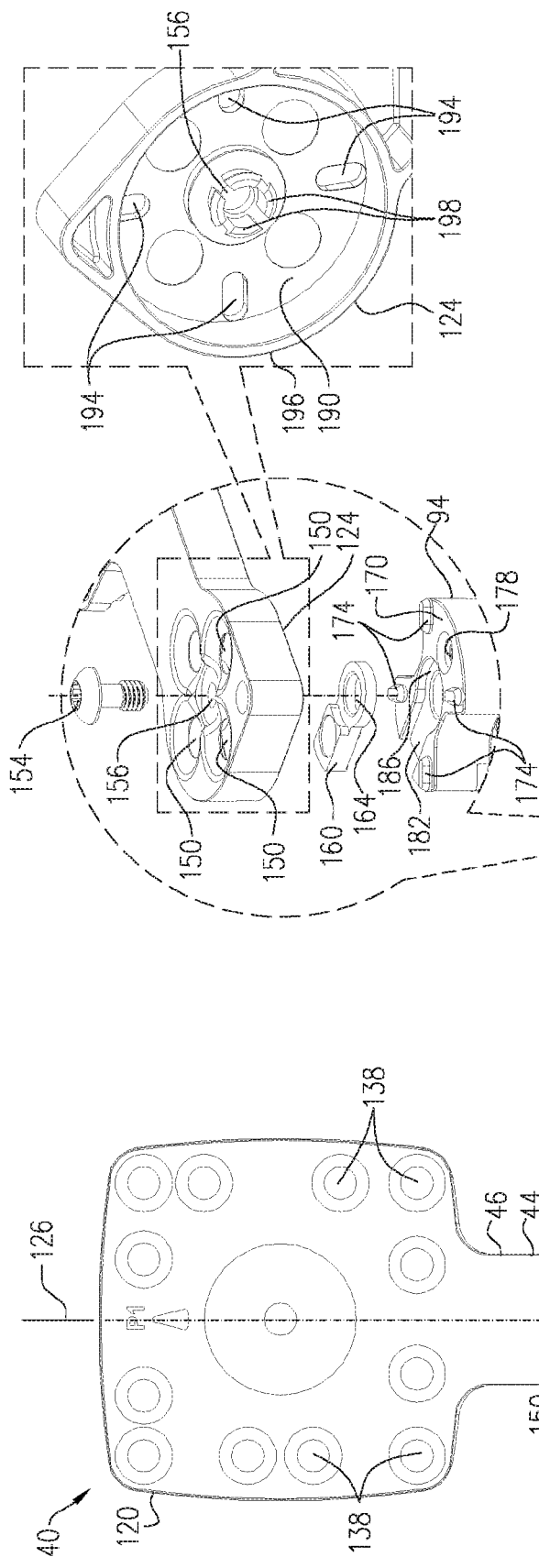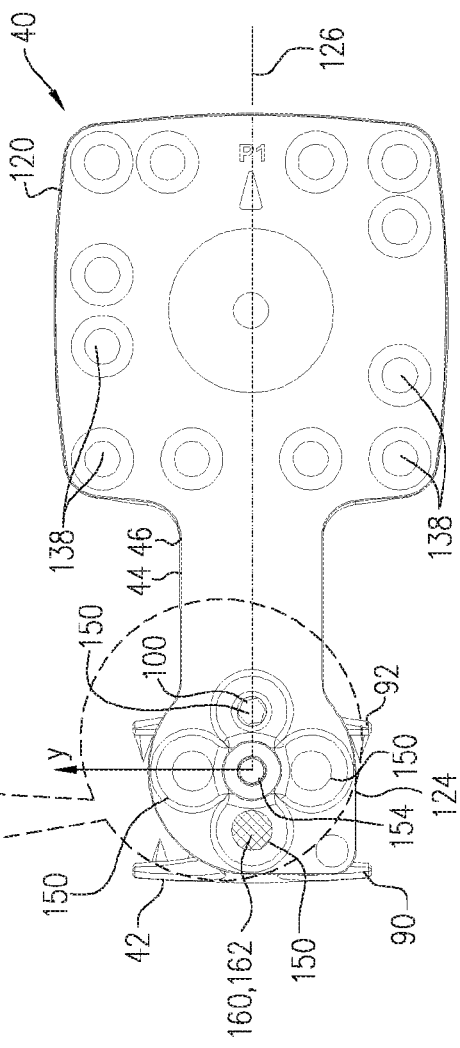
FIG. 4B
FIG. 4C

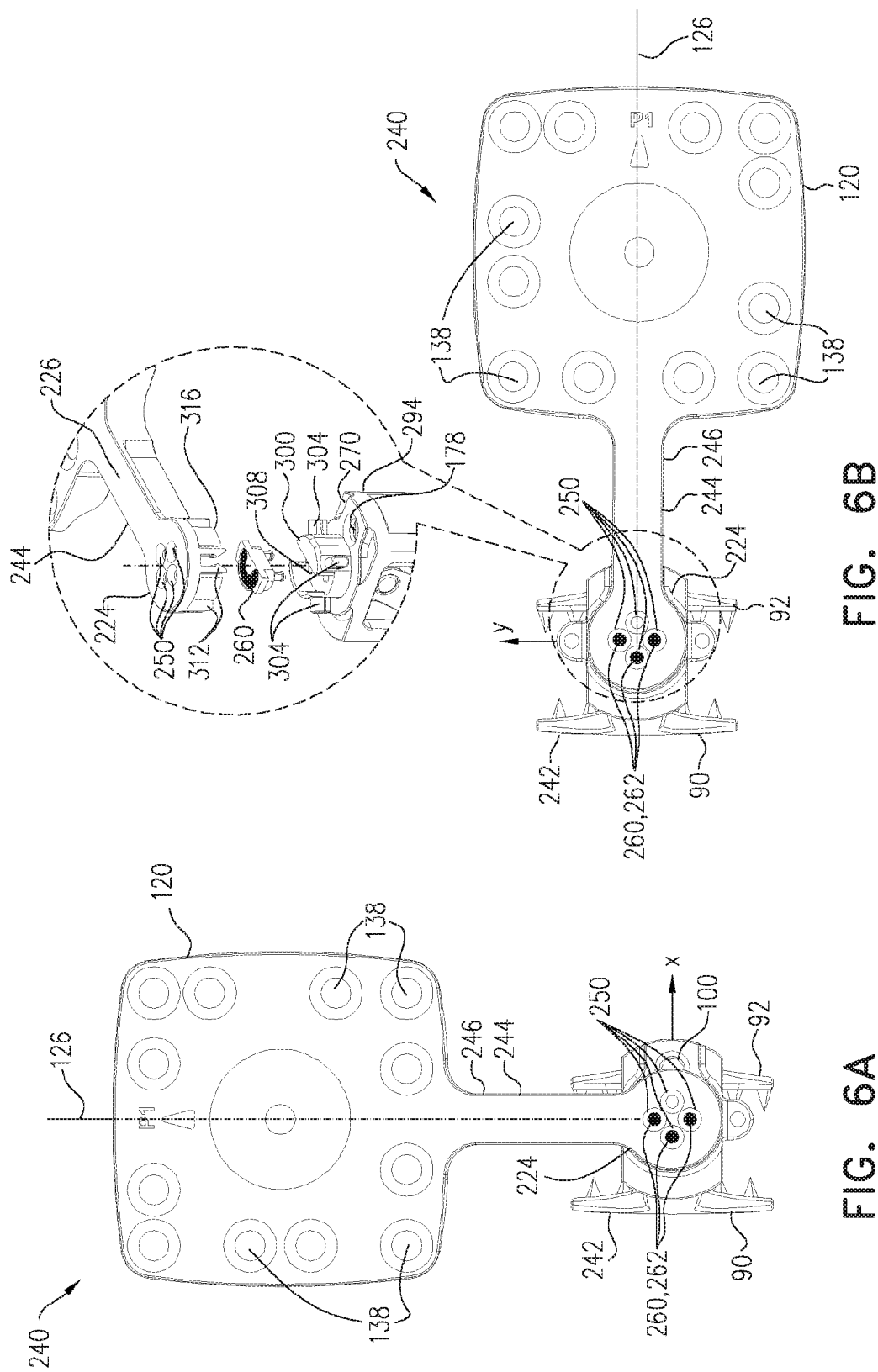

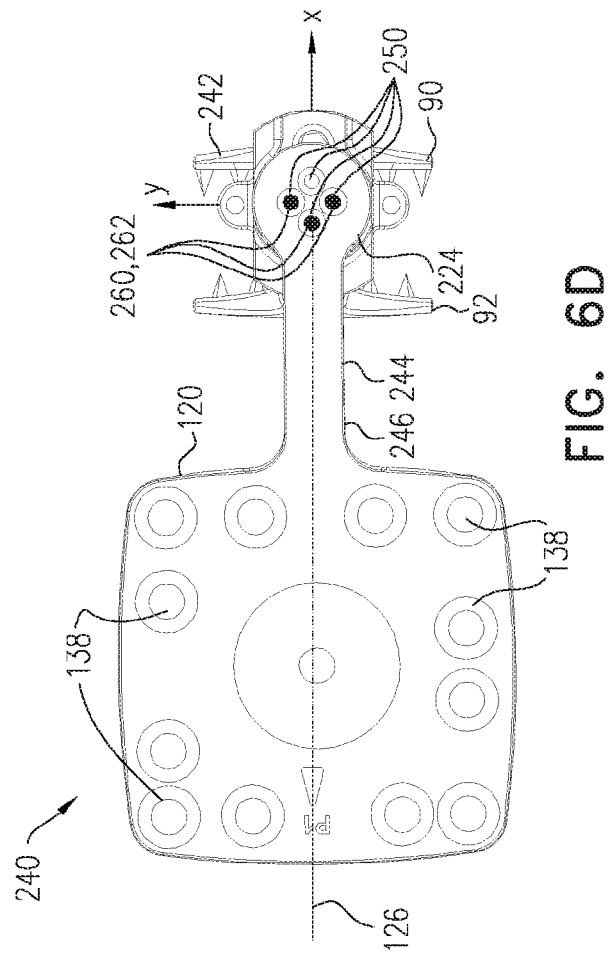
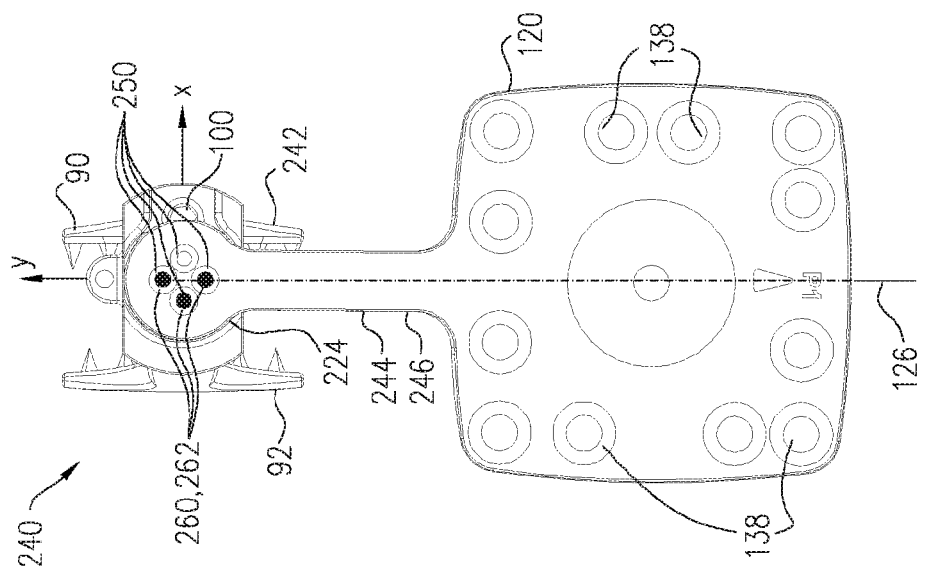
FIG. 6D
FIG. 6C

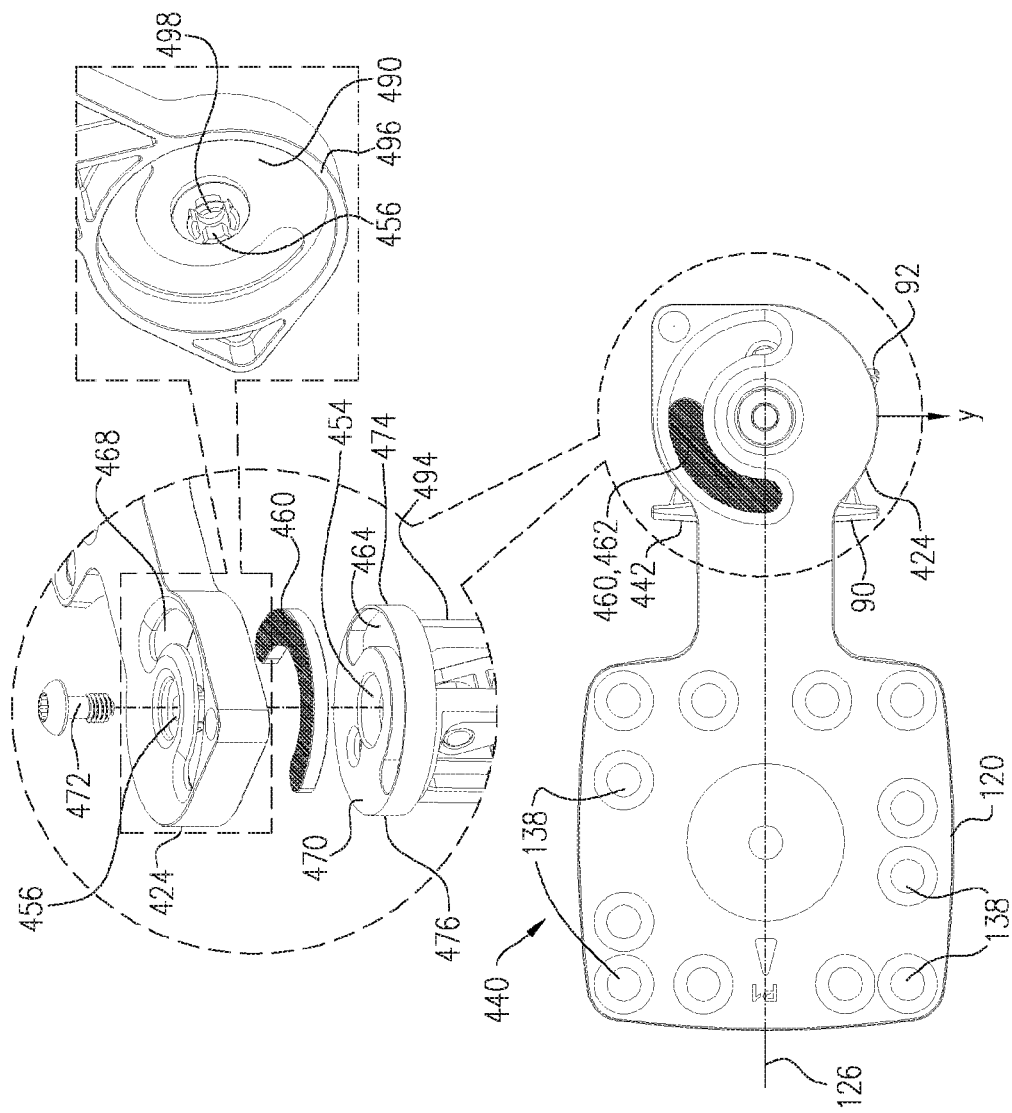
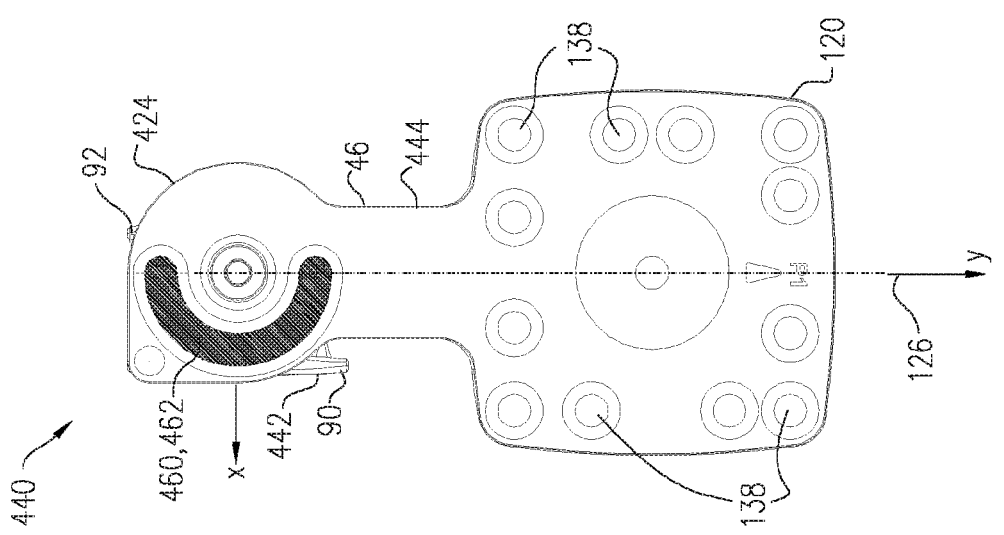
FIG. 7B
FIG. 7A

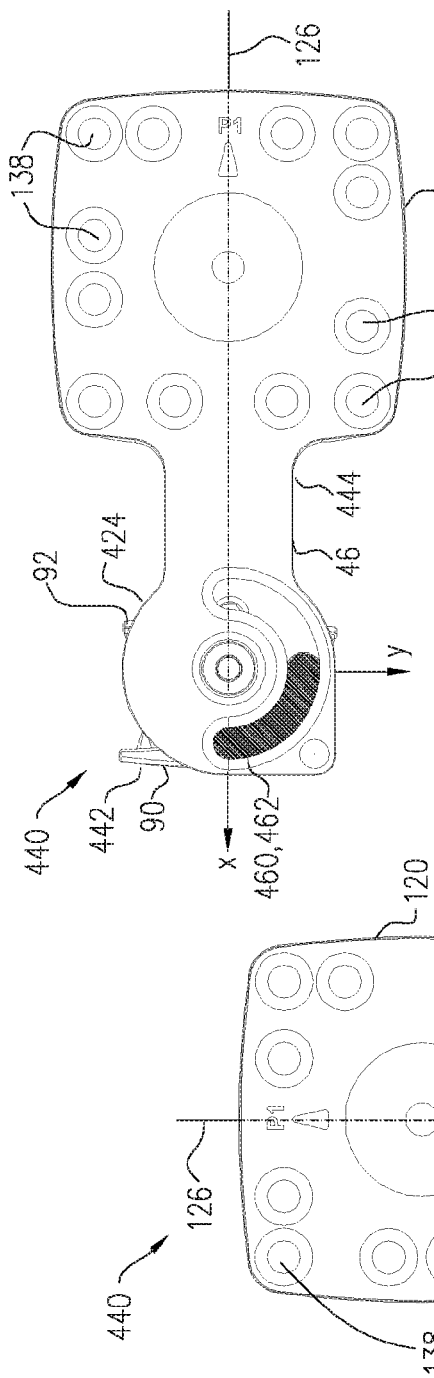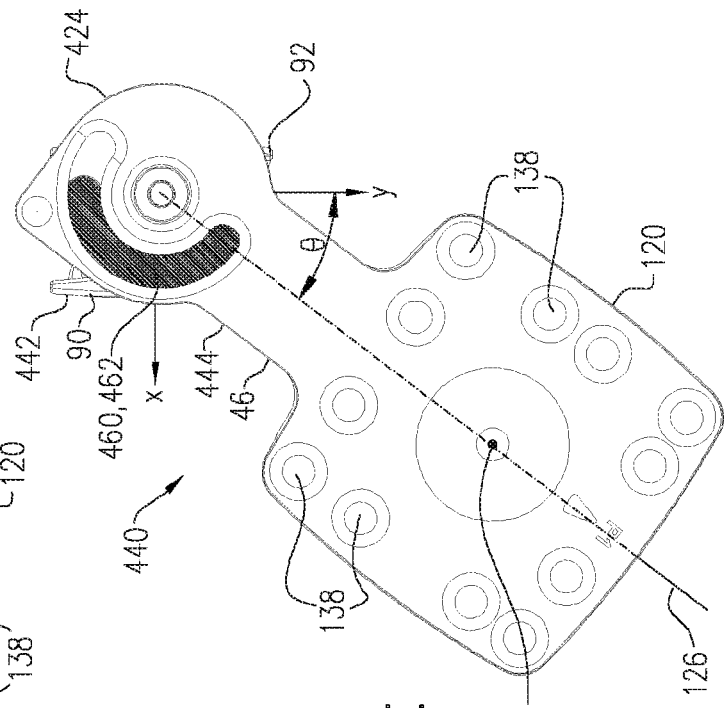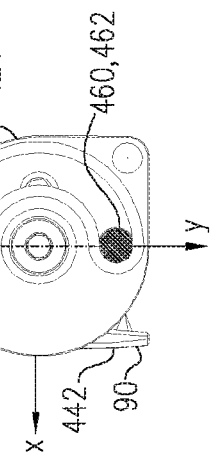
FIG. 7C
FIG. 7D
FIG. 7E

ROTATING MARKER FOR IMAGE GUIDED SURGERY

FIELD OF THE INVENTION

The present invention relates generally to surgery, and specifically to surgery performed using augmented reality.

BACKGROUND OF THE INVENTION

In an augmented reality system used by a physician performing surgery, it is typically necessary to register a frame of reference of a patient with a frame of reference of the augmented reality system used by the physician. Methods for registration are known in the art.

U.S. Pat. No. 8,848,977 to Bammer et al., describes a method for optical pose detection. A self-encoded marker where each feature on the pattern is augmented with a 2-D barcode is provided.

U.S. Pat. No. 9,220,573 to Kendrick et al., describes a system for tracking a tracking device for use with a surgical navigation system. The system can include at least one tracking device having a plurality of faces, and the faces can be operable to generate a signal upon activation.

U.S. Pat. No. 9,378,558 to Kajiwara et al., describes a self-position/self-orientation calculation unit calculating self-position and/or self-orientation in a predetermined coordinate system based on a marker in acquired imaged image data when it is determined that the marker exists within a predetermined area.

U.S. Pat. No. 9,495,585 to Bicer et al., describes methods to find one to one mapping between fiducial markers on a tracked object and fiducial marker projections on an image plane captured by a camera in optical object tracking systems.

U.S. Pat. No. 9,943,374 to Merritt et al., describes an image guidance system for tracking a surgical instrument during a surgical procedure. The image guidance system includes a plurality of cameras adapted to be located external to a surgical area for capturing images of optically visible patterns.

U.S. Pat. No. 10,022,104 to Sell et al., describes a marker that includes a first marker component having a first hydrogen proton density and a first mass density; and a second marker component having a second hydrogen proton density different than the first hydrogen proton density.

U.S. Pat. No. 10,080,616 to Wilkinson et al., describes a system which generates a three-dimensional representation of a bone and reference markers, defines a coordinate system for the three-dimensional representation, and determines locations of the reference markers relative to the coordinate system.

U.S. Pat. No. 10,108,833 to Hong et al., describes a marker with a pattern formed thereon, and which includes an optical system. At least a part of the pattern that uniquely appears depending on a direction in which the pattern is viewed from outside of the marker, through the optical system, is visually identified from the outside of the marker.

U.S. Pat. No. 10,251,724 to McLachlin et al., describes a reference tie that may be secured around a portion of a spine during a surgical procedure and that may be tracked by a surgical navigation system.

U.S. Pat. No. 10,296,805 to Yang et al., describes a marker wherein at least one of a position and pose with respect to a capturing unit is estimated.

U.S. Pat. No. 10,420,626 to Tokuda et al., describes methods for automated detection and registration of medical images using fiducial markers and processing algorithms.

U.S. Pat. No. 10,463,434 to Siegler et al., describes tracking marker support structures that include one or more fiducial reference markers, where the tracking marker support structures are configured to be removably and securely attached to a skeletal region of a patient.

U.S. Pat. No. 10,504,231 to Fiala describes fiducial markers that are printed patterns detected by algorithms in imagery from image sensors for applications such as automated processes and augmented reality graphics.

U.S. Pat. No. 10,537,395 to Perez describes a kinematic connector assembly for kinematically coupling two objects. The kinematic connector assembly comprises a receiver defining a cavity and having a plurality of constraint surfaces accessible in the cavity.

U.S. Patent Application 2003/0210812 to Khamene et al., describes an apparatus for pose determination using single camera tracking in a workspace The apparatus includes a computer programmed for making the pose determination and a tracker camera coupled to the computer for providing a tracking image and for which calibration information is stored.

U.S. Patent Application 2011/0098553 to Robbins et al., describes automatic registration of a magnetic resonance (MR) image that is carried out in an image guidance system by placing MR visible markers at known positions relative to markers visible in a camera tracking system.

U.S. Patent Application 2013/0106833 to Fun describes an input device for providing three-dimensional, six-degrees-of-freedom data input to a computer. The device includes a tracker having tracking points. One array of tracking points defines a first axis. Another array defines a second axis or plane orthogonal to the first axis.

U.S. Patent Application 2015/0150641 to Daon et al., describes a three-dimensional position and orientation tracking system that comprises one or more pattern tags, each comprising a plurality of contrasting portions, and a tracker for obtaining image information about the pattern tags.

U.S. Patent Application 2016/0324583 to Kheradpir et al., describes a patient reference device that includes a housing having a back side and a front side, and at least three tracking markers attached to the front side of the housing. The housing extends around the at least three tracking markers and beyond a horizontal plane defined by tops of the at least three tracking markers.

U.S. Patent Application 20170239015 to Sela et al., describes an apparatus that is at least partially visible by both a three dimensional (3D) scanner system of a medical navigation system and a tracking system of the medical navigation system.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a marker for image guided surgery, including:

a base, having a base axis, connecting to a clamp; and an alignment target, including:

a target region having an alignment pattern formed thereon;

a socket connected to the target region and configured to fit rotatably to the base, whereby the alignment target is rotatable about the base axis; and an optical indicator for the socket indicating an angle of orientation of the alignment target about the base axis.

In a disclosed embodiment the socket is configured to only fit to the base in a plurality of at least two discrete orientations about the base axis. Typically, the plurality of discrete configurations is distributed symmetrically about the base axis. The plurality may consist of four discrete orientations.

In a further disclosed embodiment the socket consists of a plurality of apertures equal to the plurality of discrete orientations, and the optical indicator is configured to be visible through one of the apertures indicative of one of the discrete orientations.

In a yet further disclosed embodiment the socket consists of a plurality of apertures equal to the plurality of discrete orientations, and the optical indicator is configured to be visible through apertures selected and arranged so as to provide an unambiguous identification of each of the discrete orientations.

In an alternative embodiment the socket is configured to fit to the base in a plurality of non-discrete orientations about the base axis. The socket may include an aperture, and the optical indicator may be congruent with the aperture, and a fraction of the optical indicator visible through the aperture may be indicative of one of the non-discrete orientations. The aperture may consist of a semicircular arc.

In a further alternative embodiment the socket is at a fixed distance from the target region, and the marker further includes:

an augmented reality system operative during surgery on a patient; and a processor configured to:

track the alignment target during the surgery, provide a patient tracking vector to the augmented reality system in response to the tracking of the alignment target, calculate a change in the angle of orientation of the alignment target in response to changes in images of the optical indicator, and add a change-of-orientation vector, based only on the fixed distance and the change in the angle of orientation, to the patient tracking vector so as to update the patient tracking vector.

An embodiment of the present invention also provides a method for enabling rotation of a marker during surgery without requiring re-registration, including:

connecting a base, having a base axis, to a clamp;

forming an alignment pattern on a target region of an alignment target;

connecting a socket to the target region, the socket being at a fixed distance from the target region and being configured to fit rotatably to the base, whereby the alignment target is rotatable about the base axis;

providing an optical indicator for the socket indicating an angle of orientation of the alignment target about the base axis;

operating an augmented reality system during the surgery on a patient;

tracking the alignment target during the surgery;

providing a patient tracking vector to the augmented reality system in response to the tracking of the alignment target;

calculating a change in the angle of orientation of the alignment target in response to changes in images of the optical indicator; and adding a change-of-orientation vector, based only on the fixed distance and the change in the angle of orientation, to the patient tracking vector so as to update the patient tracking vector.

In accordance with aspects of the present disclosure, a marker for image guided surgery is disclosed, the marker includes a base, having a base axis, connecting to an anchoring device; and an alignment target, including: a target region having an alignment pattern formed thereon; a socket connected to the target region and configured to fit rotatably to the base, whereby the alignment target is rotatable about the base axis; and an optical indicator for the socket indicating an angle of orientation of the alignment target about the base axis.

In various embodiments of the marker, the socket is configured to only fit to the base in a plurality of at least two discrete orientations about the base axis.

In various embodiments of the marker, the plurality of discrete configurations is distributed symmetrically about the base axis.

In various embodiments of the marker, the plurality comprises four discrete orientations.

In various embodiments of the marker, the socket comprises a plurality of apertures equal to the plurality of discrete orientations, and the optical indicator is configured to be visible through one of the apertures indicative of one of the discrete orientations.

In various embodiments of the marker, the socket comprises a plurality of apertures equal to the plurality of discrete orientations, and the optical indicator is configured to be visible through apertures selected and arranged so as to provide an unambiguous identification of each of the discrete orientations.

In various embodiments of the marker, the socket is configured to fit to the base in a plurality of non-discrete orientations about the base axis.

In various embodiments of the marker, the socket comprises an aperture, and the optical indicator is congruent with the aperture, and a fraction of the optical indicator visible through the aperture is indicative of one of the non-discrete orientations.

In various embodiments of the marker, the aperture comprises a semicircular arc.

In accordance with aspects of the present disclosure, an augmented reality system or a navigation and/or tracking system operative during surgery on a patient is provided, the system includes the marker, wherein the socket is at a fixed distance from the target region; and a processor configured to or a storage medium storing machine-executable instructions configured to execute on a computing system the instructions, when executed, cause the computing system to: track the alignment target during the surgery, provide a patient tracking vector in response to the tracking of the alignment target, calculate a change in the angle of orientation of the alignment target in response to changes in images of the optical indicator, and add a change-of-orientation vector, based only on the fixed distance and the change in the angle of orientation, to the patient tracking vector so as to update the patient tracking vector.

In various embodiments of the marker, the marker further includes the anchoring device.

In various embodiments of the marker, the anchoring device is a clamp or a pin.

In accordance with aspects of the present disclosure, a marker for image guided surgery is provided, the marker includes: a base, having a base axis; an interface configured to be coupled to an anchoring device; and an alignment target including: a target region having an alignment pattern formed thereon; a socket connected to the target region and configured to fit rotatably to the base, whereby the alignment target is rotatable about the base axis; and an optical indicator for the socket indicating an angle of orientation of the alignment target about the base axis.

In various embodiments of the marker, the base comprises the interface.

In various embodiments of the marker, the interface is coupled to the anchoring device in a manner that aligns the base axis with a base axis of the anchoring device.

In accordance with aspects of the present disclosure, a method for enabling rotation of a marker during surgery without requiring re-registration is provided, the method includes: connecting a base, having a base axis, to an anchoring device; forming an alignment pattern on a target region of an alignment target; connecting a socket to the target region, the socket being at a fixed distance from the target region and being configured to fit rotatably to the base, whereby the alignment target is rotatable about the base axis; providing an optical indicator for the socket indicating an angle of orientation of the alignment target about the base axis; operating an augmented reality system during the surgery on a patient; tracking the alignment target during the surgery; providing a patient tracking vector to the augmented reality system in response to the tracking of the alignment target; calculating a change in the angle of orientation of the alignment target in response to changes in images of the optical indicator; and adding a change-of-orientation vector, based only on the fixed distance and the change in the angle of orientation, to the patient tracking vector so as to update the patient tracking vector.

In various embodiments of the method, the socket is configured to only fit to the base in a plurality of at least two discrete orientations about the base axis.

In various embodiments of the method, the method further includes the socket includes a plurality of apertures equal to the plurality of discrete orientations, and wherein the optical indicator is configured to be visible through one of the apertures indicative of one of the discrete orientations.

In various embodiments of the method, the socket includes a plurality of apertures equal to the plurality of discrete orientations, and wherein the optical indicator is configured to be visible through apertures selected and arranged so as to provide an unambiguous identification of each of the discrete orientations.

In various embodiments of the method, the socket is configured to fit to the base in a plurality of non-discrete orientations about the base axis.

In various embodiments of the method, the socket includes an aperture, and wherein the optical indicator is congruent with the aperture, and wherein a fraction of the optical indicator visible through the aperture is indicative of one of the non-discrete orientations.

In accordance with aspects of the present disclosure, a computer-implemented method for enabling rotation of a marker during surgery without requiring re-registration, wherein the marker is anchored to a patient and configured to fit rotatably to a base, and wherein the marker comprises an alignment pattern and an optical indicator, the optical indicator configured to indicate an angle of orientation of the marker about a base axis of the base and the optical indicator is being at a fixed distance from the alignment pattern, the method including: operating a navigation system during the surgery on the patient; tracking the alignment target during the surgery; providing a patient tracking vector to the navigation system in response to the tracking of the alignment target; calculating a change in the angle of orientation of the alignment target in response to changes in images of the optical indicator; and adding a change-of-orientation vector, based only on the fixed distance and the change in the angle of orientation, to the patient tracking vector so as to update the patient tracking vector.

The present disclosure will be more fully understood from the following detailed description of the embodiments thereof, taken together with the drawings, in which:

BRIEF DESCRIPTION OF THE DRAWINGS

FIGS. 4B-4E are schematic views of different orientations of the marker, according to an embodiment of the present invention;

FIGS. 6A-6D are schematic views of different orientations of an alternative patient marker, according to an embodiment of the present invention;

FIGS. 7A-7E are schematic views of different orientations of another alternative patient marker, according to an embodiment of the present invention;

DETAILED DESCRIPTION OF EMBODIMENTS

Overview

Figure 1:
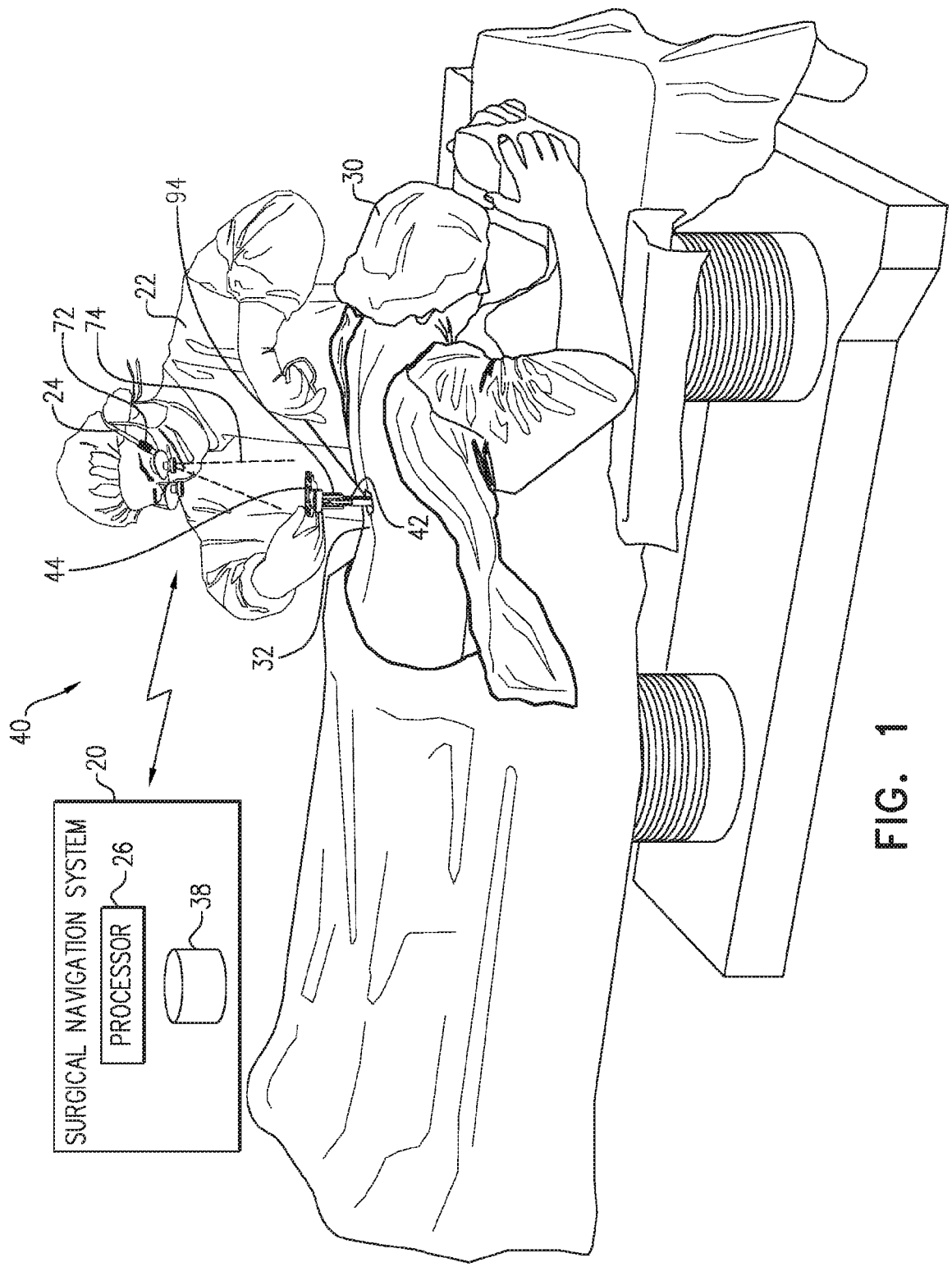
FIG. 1, which is a schematic illustration of a medical procedure, according to an embodiment of the present invention.

In an augmented reality system that is used during surgery or a medical procedure on a patient it is necessary to track the position or movement (or both) of the patient. The system typically comprises a head-mounted display worn by a professional performing the surgery, and the tracking performed e.g., via a tracking system, is required so as to maintain registration of images of the patient that are presented in the display with the professional's view of the patient.

To track the patient's position or movement relative to the display, an alignment target (may be also referred as "target"

herein below) may be fixed to the patient and a processor (e.g., via a tracking system) may be configured to track or determine the relative location of the target. In embodiments of the invention the target is fixed to a base of a patient anchoring device such as a clamp or a pin that is clamped or inserted to a bone of the patient, so that the target, when attached to the patient anchoring device, e.g., a clamp base, acts as a patient marker. According to other embodiments of the invention, the patient marker comprises the alignment target coupled to a marker base, wherein the patient marker may be anchored to the patient via an anchoring device, such as a clamp (e.g., a base of the anchoring device). If the surgery is on the spine of the patient, the bone may comprise one or more spinous processes of the patient's vertebrae.

Typically, the tracked position or location of the target of the patient marker is "registered" with or represents the patient (e.g., utilized as a fiducial marker), and this "registration" or representation is used by the processor during the surgery. Tracking or determining of the target location allows maintaining the registration of images of the patient that are presented in the display with the professional's view of the patient and may further allow the display of other tracked elements on the images of the patient, such as tools used during the surgery. The display of the tools may facilitate their navigation by the professional performing the surgery.

However, during the procedure the alignment target may interfere with the surgery being performed, for example, by obstructing the professional's view and/or by restricting the professional's action. In this case, the alignment target may be re-oriented or re-positioned with respect to the anchoring device, e.g., a clamp, and/or the patient, e.g., by re-positioning the target and/or the clamp, to overcome the interference. The re-orientation or re-positioning, may be performed by detaching the target from the clamp, then re-attaching the target to the clamp, or by re-positioning of the clamp itself. The above may necessitate re-registration of the target with the clamp, re-positioning of the clamp with respect to the bone and/or even the performance of an additional incision.

Embodiments of the present invention allow for re-orientation of the target with respect to the patient anchoring device without the necessity of re-registration by the professional and/or the performance of any additional operations. The alignment target comprises a target region having an alignment pattern formed thereon. A socket comprised in the alignment target is fixedly connected at a known distance to the target region. The alignment target and/or the anchoring device base also comprises an optical indicator for the socket indicating an angle of orientation of the alignment target about the base axis. According to some aspects, the socket is configured to fit rotatably to the base of the anchoring device, e.g., a clamp, so that the alignment target is rotatable about a base axis defined by the clamp base. According to some aspects, the patient marker comprises an alignment target coupled to a marker base. The alignment target comprises the optical indicator and configured to rotate around an axis of the marker base.

During the procedure the processor operating the augmented reality system may track the alignment target so as to provide a patient tracking vector to the system, the vector maintaining the registration referred to above. The processor may then calculate a change in the angle of orientation of the alignment target in response to changes in images of the optical indicator. Based only on the change in the angle of orientation and the known target region-socket distance, the processor may calculate a change-of-orientation vector, and then add this vector to the patient tracking vector so as to update the patient tracking vector.

The updated patient tracking vector acts to automatically update the registration of the tracking of the alignment target, indicating the professional's view of the patient, with the patient image data, so that no re-registration and/or any additional operations are necessary.

The terms "position" and "location" may be hereby interchangeably used. Although the description refers to a surgery, the disclosed systems, devices, and methods may be applicable, mutatis mutandis, to any suitable medical procedure. Although the description refers to a spinal surgery or a spinal medical procedure, the disclosed systems, devices, and methods may be applicable, mutatis mutandis, to medical procedures performed with respect to structures or parts of the body other than the spine, including joint trauma related procedures, hip surgery and hip replacement or cranial procedures. Although the description refers to a clamp, the disclosed systems, devices, and methods may be applicable, mutatis mutandis, to any other patient or bone anchoring device, such as a pin inserted into a patient's bone, e.g., into the ilium or a cranial anchoring frame. Although the description refers to an augmented reality system, the disclosed systems, devices and methods may be applicable, mutatis mutandis, to other navigation and/or tracking and display systems, such as stationary tracking and/or display systems, which are not head-mounted, and the like.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic illustration of a medical procedure, according to an embodiment of the present invention. During the procedure, performed by a professional 22, the professional uses a surgical navigation system 20, which assists the professional in performance of the procedure. Surgical navigation system 20 comprises a processor 26, which operates elements of the system, and which communicates with an augmented reality assembly 24, worn by professional 22, that is incorporated in the system. While assembly 24 may be incorporated for wearing into a number of different retaining structures on professional 22, in the present description the retaining structure is assumed to be similar to a pair of spectacles. Those having ordinary skill in the augmented reality art will be aware of other possible structures, such as incorporation of the augmented reality assembly into a head-up display that is integrated into a helmet worn by the user of system 20, and all such structures are assumed to be comprised within the scope of the present invention.

In one embodiment processor 26 is assumed to be incorporated within a stand-alone computer, and the processor typically communicates with other elements of the system, including assembly 24, wirelessly, as is illustrated in FIG. 1. Alternatively or additionally, processor 26 may use optical and/or conducting cables for the communication. In further alternative embodiments processor 26 is integrated within assembly 24, or in the mounting of the assembly. Processor 26 is typically able to access a database 38, wherein are stored images, other visual elements and any other type of data, including computer code, used by system 20. Software enabling processor 26 to operate system 20 or assembly 24

(or both) may be downloaded to the processor or to database 38 in electronic form, over a network, for example. Alternatively or additionally, the software may be provided on non-transitory tangible media, such as optical, magnetic, or electronic storage media.

Assembly 24 comprises, inter alia, an image capturing device 72, also termed herein a camera 72, that has a field of view 74. Camera 72 may be configured to capture images in the visible spectrum, non-visible spectrum or both. Assembly 24 and functions of system 20, processor 26, and device 72 are described below. An assembly similar to augmented reality assembly 24, and its operation, are described in U.S. Pat. No. 9,928,629, to Benishti, et al., whose disclosure is incorporated herein by reference.

The medical procedure exemplified here is performed on a patient 30, and during an initial stage of the procedure professional 22 makes an incision 32 into the patient's back. The professional then inserts a spinous process clamp 42, into the incision, so that opposing jaws of the clamp are located on opposite sides of a spinous process. The professional adjusts clamp 42 to grip one or more spinous processes, selected by the professional, of the patient.

The professional attaches an alignment target 44 to a base 94 of the clamp, the target when attached to the base operating as a patient marker 40. Patient marker 40 thus comprises alignment target 44 coupled to base 94. As is described below, patient marker 40 is used by system 20 to determine the position and orientation of patient 30 during the medical procedure.

Figure 2:
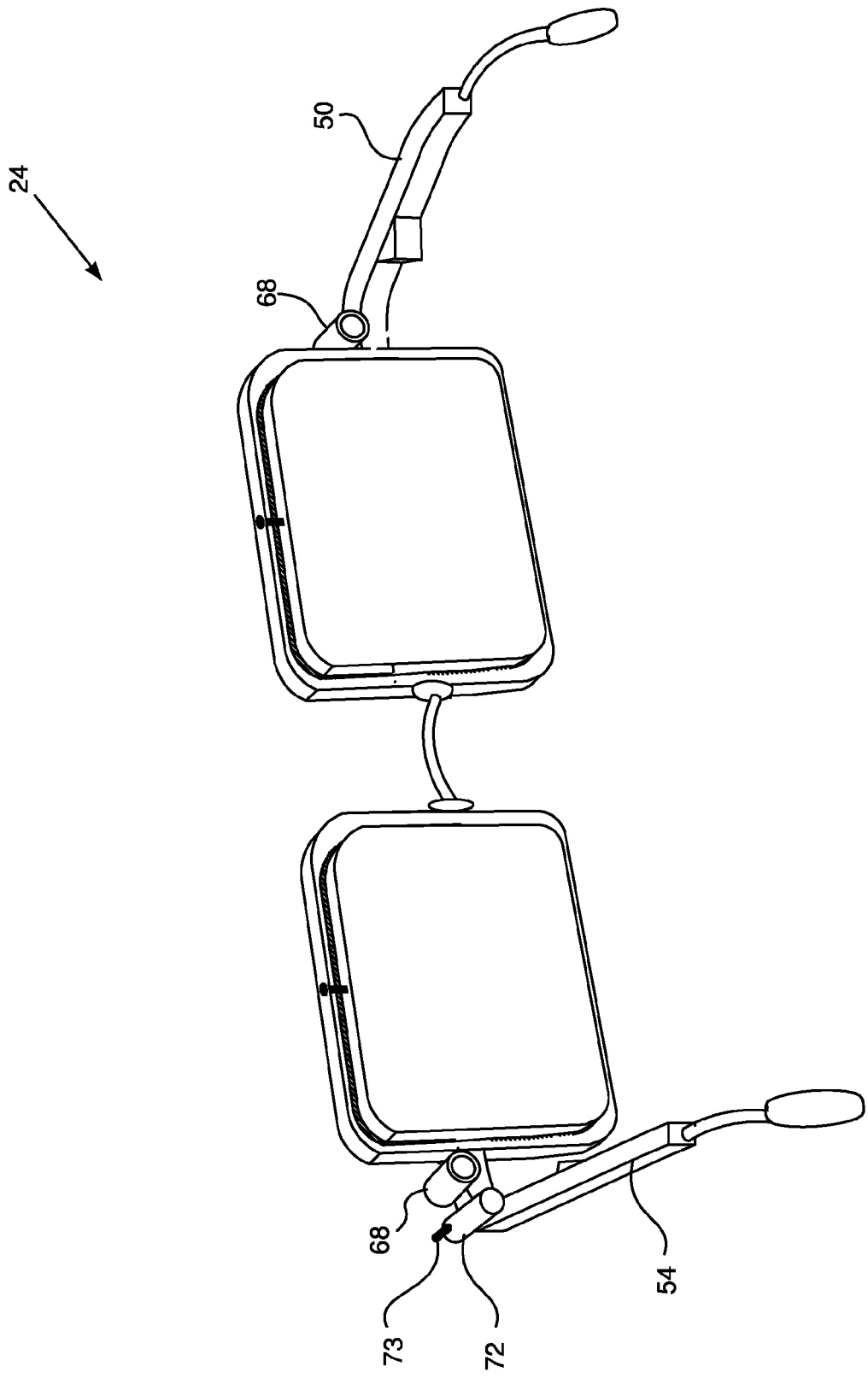
FIG. 2 is a schematic diagram illustrating an exemplary augmented reality assembly used in the procedure, according to an embodiment of the present invention.

FIG. 2 is a schematic diagram illustrating assembly 24, according to an embodiment of the present invention. As stated above, assembly 24 is configured, by way of example, as a pair of spectacles 50 mounted on a frame 54.

At least one image capturing device 68 or 72 is attached to frame 54. Typically, devices 68 comprise cameras configured to capture images of scenes viewed by the professional's eyes, including images of marker 40 in the visible spectrum.

As stated above assembly 24 comprises camera 72, which is configured to capture images of elements of a scene, including marker 40, in front of assembly 24. The images are produced from radiation projected by a projector 73 that is in the spectrum detected by camera 72. Projector 73 is located in close proximity to camera 72, so that radiation from the projector, that has been retroreflected, is captured by camera 72. The camera typically has a bandpass filter configured to block other radiation, such as that projected by surgical lighting. Typically, camera 72 and projector 73 operate in a non-visible region of the spectrum, such as in the near infra-red spectrum. As is described below, at least some retroreflected radiation is typically received from marker 40, and processor 26 uses the image of the marker produced by camera 72 from the received radiation to track the marker, and thus the position and orientation of patient 30. By tracking the position and orientation of patient 30, the processor is able to present, to professional 22 in assembly 24, images of the patient (e.g., a Computerized Tomography scan) that are correctly registered with the physician's actual view of the patient.

According to some aspects, camera 72 may be mounted on frame 54 between the two lenses of spectacles 50. According to some aspects, projector 73 may include two or more projectors. According to another exemplary embodiment, assembly 24 comprises only one capturing device, e.g., camera 72, configured to operate in the non-visible region of the spectrum, such as in the near infra-red spectrum. Camera 72 may be then configured to capture images of scenes viewed by the professional's eyes, including images of marker 40 in the non-visible spectrum. According to some aspects, camera 72 and two projectors 73 may be mounted on frame 54 between the two lenses of spectacles 50. Each of projector 73 may be mounted on each side of camera 72.

Capturing devices 68 and/or 72 and projector 73 may be mounted or positioned on other positions or arranged in other configurations with respect to frame 54 than as illustrated and described with respect to FIGS. 1 and 2, and as may be practiced, implemented or envisioned by persons skilled in the art.

Figure 3:
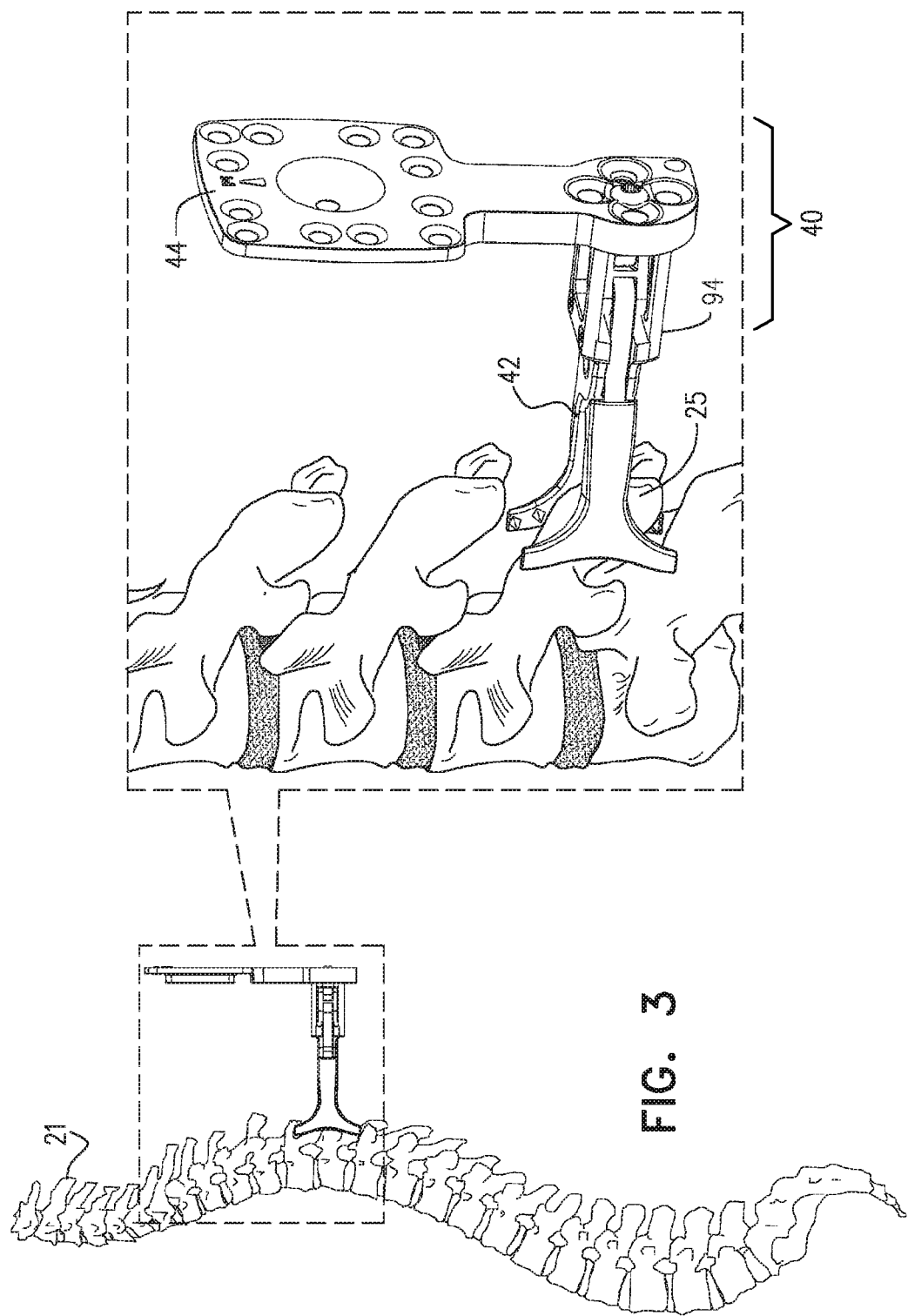
FIG. 3 schematically illustrates the situation after an exemplary patient marker has been attached to an exemplary clamp which is inserted and adjusted in a patient, according to an embodiment of the present invention.

FIG. 3 schematically illustrates the situation after clamp 42 has been inserted and adjusted in patient 30, according to an embodiment of the present invention. Target 44 is then attached to base 94 of the clamp, forming marker 40. The figure illustrates that clamp 42 has been attached to grip a bone 21 of patient 30, specifically to grip a spinous process 25 of vertebrae of the spine of the patient. After attachment, alignment target 44 is external to the patient. As shown in FIG. 3, exemplary clamp 42 comprises teeth, protruding internally from jaws of the clamp, the teeth facilitating the clamp fixedly gripping the spinous processes. An exemplary configuration of marker 40 is described in more detail below with reference to FIGS. 4A-4E.

Figure 4A:
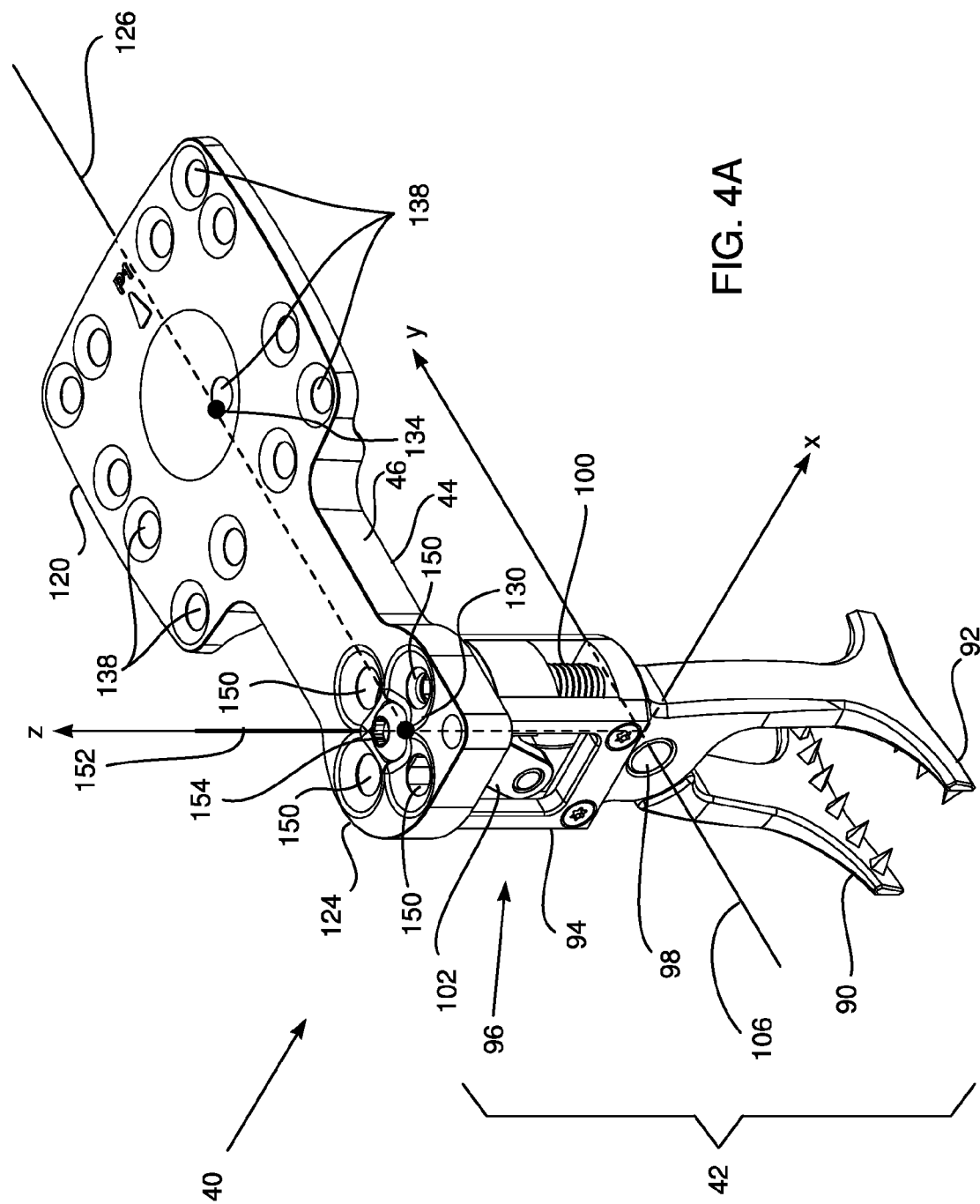
FIG. 4A is a schematic perspective view of the marker.
Figure 4E:
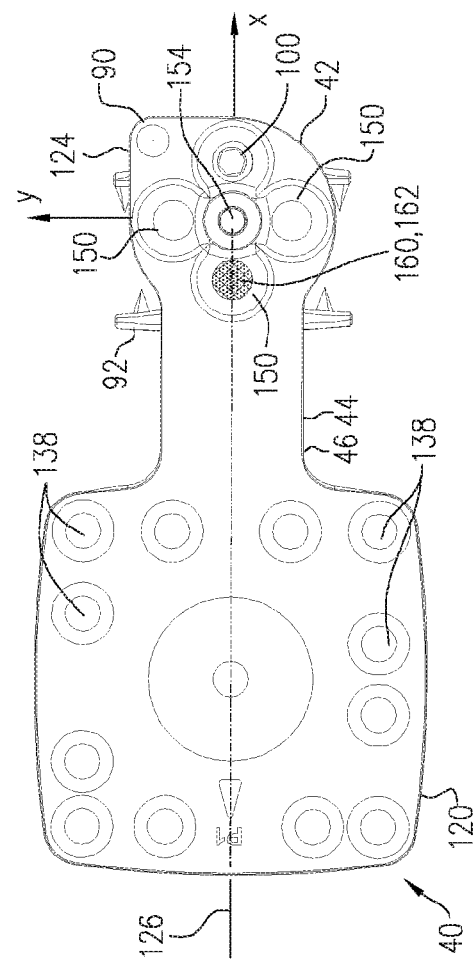
Figure 4D:
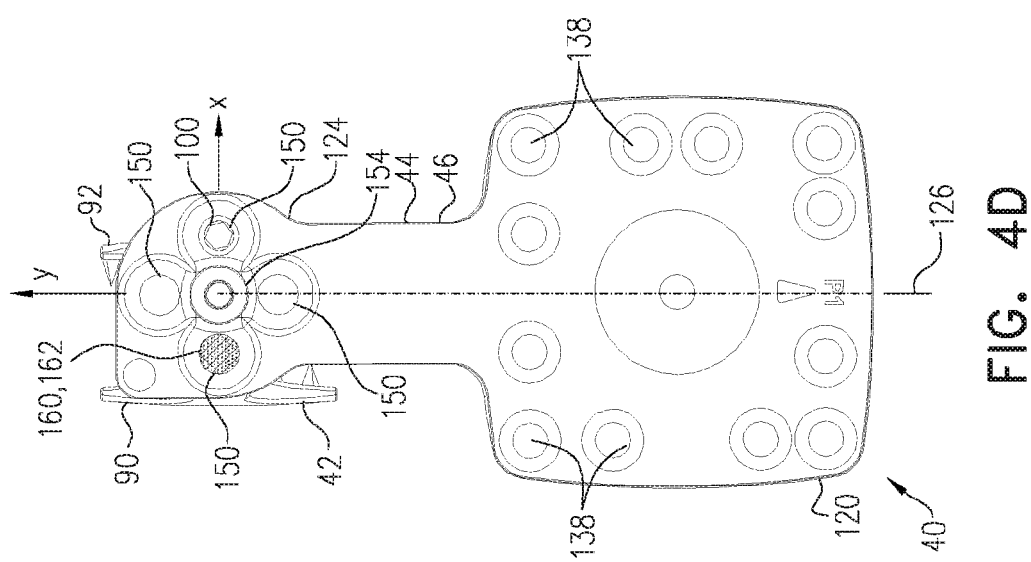

FIG. 4A is a schematic perspective view of marker 40, and FIGS. 4B-4E are schematic views of different orientations of the marker, according to an embodiment of the present invention. As stated above, marker 40 is formed by attaching alignment target 44 to base 94 of clamp 42. The clamp is described below.

Exemplary clamp 42 comprises a pair of jaws 90, 92 in a lower section of the clamp. The jaws are coupled to clamp base 94 in an upper section of the clamp, the base comprising a jaw adjustment mechanism 96. In the embodiment described herein, jaw 92 is fixed to base 94, and jaw 90 moves with respect to jaw 92, by being rotated about a hinge pin 98. Jaw adjustment mechanism 96 comprises an adjustment screw 100, which is coupled by a lever 102 to jaw 90 so that rotation of the screw causes jaw 90 to approach or retreat from jaw 92. Thus professional 22 is able to cause the jaws of clamp 42 to grip or release a bone, such as spinous process 25, by rotating screw 100. Hinge pin 98 defines a hinge axis 106 about which jaw 90 rotates, and each jaw 90, 92 is substantially parallel to the hinge axis.

For clarity, in the description herein, elements of marker 40 are assumed, by way of example, to be referenced to an xyz set of orthogonal axes, with origin at the center of hinge pin 98. The xyz set of axes is illustrated in FIG. 4A, wherein a y-axis is assumed to correspond to hinge axis 106, an x-axis is orthogonal to a plane including jaws 90 and 92, and a z-axis is orthogonal to the x- and y-axes.

Alignment target 44 comprises a target region 120 and a socket 124, the target region and the socket being fixedly connected together by a connecting rod 46. Alignment target 44, together with its components target region 120 and socket 124, are generally planar, herein termed xy planar since they are assumed to be in a plane parallel to the x- and y-axes. Embodiments of the present invention measure an angle of orientation of alignment target 44 to clamp 42, so that a line 126, constructed from a center 130 of the socket to a center 134 of the target region and extended therefrom, is herein assumed to indicate a direction of orientation of the alignment target 44.

Target region 120, by way of example, is approximately rectangular and comprises optical elements 138. Elements 138 are arranged in a three-dimensional (3D) pattern with no rotational axis of symmetry (other than a trivial axis of symmetry for rotating by 360°), and no mirror plane of symmetry, so that an image of the elements enables an unambiguous determination of the location and orientation of the target region. Elements 138 are typically retroreflectors. According to some aspects, elements 138 are arranges in a two-dimensional (2D) pattern. An entity with an arrangement of optical elements similar to the arrangement herein is described in PCT Patent Application WO2019211741A1, which is incorporated herein by reference.

As stated above, socket 124 is generally planar, and is assumed to define an axis 152 through socket center 130 and orthogonal to an xy plane. In cases where socket center 130 lies on the z-axis, axis 152 is coincident with the z-axis, as is illustrated in FIG. 4A. Socket 124 comprises four substantially similar apertures 150 which are distributed symmetrically about axis 152. Socket 124 comprises a central hole 156, and a screw 154 is configured to penetrate the hole and connect the socket to an upper surface 170 of clamp base 94, as is illustrated in the call-out of FIG. 4C. Once connected, a base axis, comprising an axis orthogonal to surface 170 through central hole 156, corresponds to axis 152.

Surface 170 is xy planar, being parallel to an xy plane, and comprises four protrusions 174 distributed symmetrically about the z-axis. There is an aperture 178 in the surface providing access to adjustment screw 100, and the positions of apertures 150 are selected so that regardless of the orientation of target 44, access to screw 100 is available through one of apertures 150. There is also a shaped indentation 182, comprising an arc 186, in surface 170, the indentation being shaped to accept a colored or retroreflective insert 160.

As is also illustrated in FIG. 4C, socket 124 comprises a planar lower surface 190, within which are inset four indents 194, distributed symmetrically about socket central hole 156, and configured to mate with protrusions 174. Surface 190 is surrounded by a circular wall 196. Extending from surface 190 are a plurality of arcs 198, also distributed symmetrically about socket central hole 156, and configured to mate with arc 186 of indentation 182.

FIGS. 4B-4E illustrate the four different discrete orientations that exemplary alignment target 44 is able to make with clamp 42, when the target is connected to the clamp with screw 154 so that socket 124 mates with base 94. Assuming that the positive y-axis of the clamp corresponds to an orientation of 0°, and those orientations are measured as clockwise rotations about the z-axis from the y-axis, FIGS. 4B, 4C, 4D, and 4E correspond respectively to the target having discrete orientations of 0°, 90°, 180°, and 270°. At each orientation arcs 198 mate with arc 186, protrusions 174 mate with indents 194, and wall 196 mates with outer circular edges of base 94, the mating ensuring that socket 124 is centered with respect to the z-axis.

As is illustrated in FIGS. 4B-4E, at each orientation insert 160 is visible through one of apertures 150, and the visible insert acts as an optical indicator 162 of the orientation. During operation of system 20, processor 26 calculates coordinates of a directed line segment between indicator 162 and center 134, the coordinates acting as an orientation metric. For each orientation there is a unique directed line segment, i.e., a unique orientation metric, so that processor 26 is able to use the calculated coordinates as an orientation indicator.

Table I below shows coordinates, the orientation metric, of the directed line segment for each of the exemplary four orientations of target 44. (For clarity, Table I, and Table II below, are drawn to a two-dimensional system, and may be adapted, mutatis mutandis, to a three-dimensional or higher system.) The coordinates are calculated assuming that indicator 162 lies on a circle radius r centered at center 130 of socket 120, and that there is a separation of D between center 130 and center 134.

TABLE I

| Orientation | Orientation Indicator Orientation Metric |
|---|---|
| 0° | (−r, 0) − (0, D) = (−r, −D) |
| 90° | (−r, 0) − (D, 0) = (−r − D, 0) |
| 180° | (−r, 0) − (0, −D) = (−r, D) |
| 270° | (−r, 0) − (−D, 0) = (D − r, 0) |

As is described herein, marker 40 is used to track the location of patient 30, typically the patient's bone, with respect to assembly 24, by tracking the location of target region 120. Since the location of the target region is fixed with respect to the patient's bone to which marker 40 is clamped, because the marker is inflexible, tracking of the patient's bone may be accomplished by tracking of the target region, and adding a fixed adjustment vector due to the differing physical positions of the target region and the bone.

Furthermore, since the target region positions have a one-to-one correlation with the orientations, and since the different target region positions are in known geometric relations to each other, these geometric relations may be pre-programmed as change-of-orientation vectors and used to continue tracking the patient when the target region orientation is changed.

For example, if target region 120 is a distance D from socket 124, then the target region positions for the orientations 0°, 90°, 180°, and 270° (illustrated in FIGS. 4B, 4C, 4D, and 4E) may be respectively represented by the two-dimensional ordered pairs (0, D), (D, 0), (0, −D), and (−D, 0). If an initial target region is in the 0° orientation, then the geometric relations, i.e., the change-of-orientation vectors, to the other three orientations are as given in Table II:

TABLE II

| New Orientation | Change-of-orientation Vector (From 0° Orientation) |
|---|---|
| 90° | (D, 0) − (0, D) = (D, −D) |
| 180° | (0, −D) − (0, D) = (0, −2D) |
| 270° | (−D, 0) − (0, D) = (−D, −D) |

It will be understood that the three change-of-orientation vectors presented in Table II do not vary with movement of marker 40. The vectors depend only on the initial and final orientation of the target region, and so, as stated above, may be pre-programmed. It will also be understood that sets of three change-of-orientation vectors from the other possible initial orientations (90°, 180°, and 270°) may be calculated as for Table II, and may also be pre-programmed.

As is explained further below, in embodiments of the present invention, when the target region orientation changes a processor adds an appropriate change-of-orientation vector to an initial tracking vector of a patient marker. This enables continuous tracking of a patient by the marker without re-registration of the marker.

Figure 5:
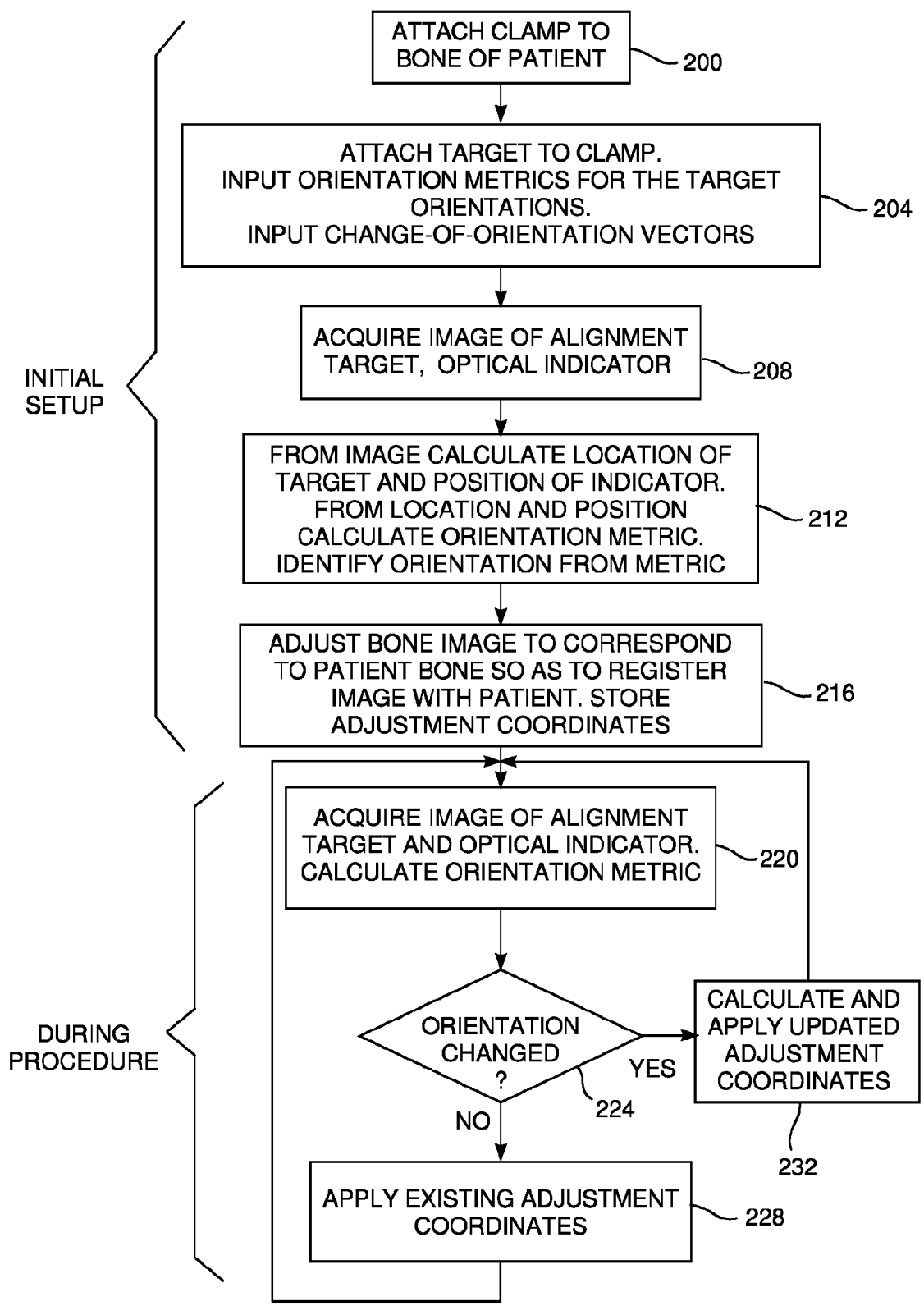
FIG. 5 is a flowchart describing the use of the marker in the medical procedure, according to an embodiment of the present invention.

FIG. 5 is a flowchart describing the use of a marker such as marker 40 in the medical procedure referred to above, according to an embodiment of the present invention.

In an initial step 200, professional 22 attaches clamp 42 or any other patient anchoring device to a bone of patient 30, herein assumed to comprise spinous process 25 of the patient, by rotating screw 100.

In a target attachment step 204, the professional attaches an alignment target to the patient anchoring device in a specific orientation. The alignment target includes an optical indicator indicating the marker current orientation. For example, alignment target 44 may be attached to the clamp, by aligning socket 124 with surface 170 of clamp base 94, and screwing screw 154. It will be understood that the attached orientation is one of the four orientations illustrated in FIGS. 4B-4E, so that after the attachment, insert 160 is visible through one of apertures 150, and acts as optical indicator 162.

The values of r and D, and the sets of orientation metrics for the orientations of the target, described above with reference to Table I, may be input to or accessed by processor 26. In addition, the sets of change-of-orientation vectors coordinates, described above with reference to Table II, may also be input to or accessed by the processor.

In an image acquisition step 208, an image of optical elements and of the optical indicator of the alignment marker is captured via the head mounted assembly. With reference to FIGS. 1 and 2, an image of optical elements 138 of target region 120 and of indicator 162, is captured, e.g., using camera 72 and/or one or more devices 68. Optionally the image may include the bone of patient 30, or of a region close to the bone, such as incision 32 and/or a tool navigated in a region close to the bone or alignment target 44. The tool may be mounted with or include a tool marker. The tool location may be then identified with respect to the patient via the tool marker and the alignment target (the patient marker).

In an analysis step 212, the processor analyzes the acquired image to identify the alignment target and/or to find a location, comprising an orientation and a position, of the alignment target.

For example, the processor analyzes the acquired image to identify and/or find a location, comprising an orientation and a position, of target region 120. The position of target region is herein, by way of example, assumed to correspond to center 134. Once the target region location has been found, the processor may initiate tracking of the target region, for example, by capturing images of the target region, e.g., once in a predefined time interval.

The processor also identifies the optical indicator of the alignment target in the acquired image. For example, processor 26 may find a position of indicator 162 in the image. From coordinates of the two positions the processor calculates coordinates of an orientation metric (as in Table I) joining the positions, and from the metrics stored in step 204, identifies the orientation of step 204.

In an adjustment step 216, the processor utilizes the image, e.g., of the bone, of the region close to the bone, and/or of a tool navigated in the region close to the bone, acquired in step 208, to generate an augmented reality display to professional 22 in augmented reality assembly 24. The professional adjusts coordinates of the presented image to correspond with the actual image visible to the professional through the assembly, and the processor stores the adjustment coordinates. The processor then applies the stored adjustment coordinates as an adjustment vector, together with the tracking of the tracked region (initiated in step 212), to the presented image, so as to register the presented image with patient 30 on a continuing basis.

The processor continues to apply the stored adjustment vector, which acts as a patient tracking vector, as long as the orientation of step 204 is unchanged. It will be understood that the registration using the stored adjustment vector counteracts any relative movement between the patient and assembly 24.

Steps 200-216 correspond to an initial setup of navigation system 20. Steps 220-232, described below, correspond to steps of the flowchart that may be implemented during the medical procedure for which system 20 is used.

In a continuing imaging step 220, an image of the alignment target and optionally of additional elements of interest (e.g., tools used during the procedure or of a region of interest on the patient's body) is continuously acquired (e.g., once in a predefined time interval). For example, an image of target 44, including target region 120 and indicator 162 is continuously acquired via assembly 24 (optionally controlled by processor 26 but not necessarily). From the images of target region 120 and indicator 162, the processor calculates an orientation metric.

In a decision step 224 the processor checks if the metric calculated in step 220 is different from that calculated in step 212, so as to check if the target region has changed orientation. If the decision returns negative, i.e., there is no change in orientation, then in a continuation step 228 the processor continues to use the existing adjustment coordinates, i.e., those of step 216.

If the decision returns positive, i.e., there is a change in orientation, then in an update step 232 the processor calculates updated adjustment coordinates, by adding the appropriate change-of-orientation vector, from step 204, to the existing adjustment coordinates. The processor applies the updated coordinates in presenting the image of the patient, e.g., of the region close to the bone, to professional 22 in augmented reality assembly 24.

It will be understood that a positive return of decision 224 is typically caused by professional 22 changing the orientation of the alignment target. The professional may change the orientation for example by unscrewing screw 154, realigning socket 124 on surface 170 so that target 44 is in a new orientation, then screwing screw 154 to fix the target in its new orientation. In some embodiments the professional may pause the tracking of target 44 while positioning target 44 in its new orientation.

The professional typically repositions target 44 to improve access to, and/or to improve visibility to, part of the patient. It will be understood that there is no need to repeat steps 200-216 after the repositioning, since the new adjustment coordinates can be calculated from the known geometric relations of the two orientations of target 44. (It will also be understood that regardless of any repositioning, adjustment screw 100 is always accessible via one of apertures 150, since the screw aligns with the apertures.) From steps 228 and 232 control returns to decision step 220, so that during the procedure the processor applies steps 220-232 iteratively.

FIGS. 6A-6D are schematic views of different orientations of a patient marker 240, according to an embodiment of the present invention. Marker 240 comprises a clamp base 294 which is coupled to an alignment target 244. Clamp base 294 is the base of a clamp 242. Apart from the differences described below, the operation of marker 240, clamp 242, base 294, and target 244 is generally similar to that of marker 40, clamp 42, base 94, and target 44, and elements indicated by the same reference numerals in both markers are generally similar in construction and in operation. As for marker 40, target 244 has four different discrete orientations with respect to clamp 242. The axes for marker 240 are as for marker 40.

In contrast to upper surface 170 of clamp base 94 of clamp 42, an upper xy surface 270 of clamp base 294 of clamp 242 is surmounted by a circular turret 300. Fixed to turret 300 are four protuberances 304, distributed symmetrically about a center of the turret, and lying in an xy plane, parallel to surface 270. Turret 300 comprises a recess 308, which is configured to accept an insert 260 that typically is colored or retroreflective.

As for socket 124, a socket 224 of target 244 comprises four apertures 250 distributed symmetrically about a center of the socket. However, socket 224 is smaller than socket 124, and regardless of target orientation, an aperture 250 does not align with screw 100. Rather, socket 224 is small enough so that in at least some target orientations, e.g. those of FIGS. 6A, 6C and 6D, screw 100 is accessible from outside the socket.

A connecting rod 246 connects target 120 to socket 224, but typically has a smaller width than rod 46.

Socket 224 has a lower circular wall 316 which has an internal surface which is configured to mate with turret 300. Set within the wall are four clips 312 which are distributed symmetrically about a center of the socket, and which are positioned to mate with protuberances 304. When clips 312 mate with protuberances 304, they hold socket 224 so that wall 316 surrounds and contacts an outer surface of turret 300, and so the socket is fixed to the turret.

Because protuberances 304 and mating clips 312 are distributed symmetrically, it will be understood that target 244 can mate with clamp 242 in one of four orientations illustrated in FIGS. 6A-6D, and that in each orientation a center of socket 224 aligns with a center of turret 300.

Unlike marker 40, where optical indicator 162 is formed from the visibility of insert 160 through one of apertures 150, in marker 240 an optical indicator 262 comprises insert 260 as viewed through three apertures 250, as illustrated in FIGS. 6A-6D.

The description of the flowchart of FIG. 5 applies to marker 240, mutatis mutandis. For example, a position of indicator 262 may be assumed to be the position of the central one of the three apertures 260.

Markers 40 and 240 each have four symmetrically distributed discrete orientations. However, embodiments of the present invention may have other numbers of symmetrically distributed orientations, where the number may be as little as two.

The number of apertures 150 corresponds to the number of discrete orientations. As exemplified by indicator 162 the number of apertures used to generate the optical indicator may be a single aperture. Alternatively, as exemplified by indicator 262, the number of apertures used to generate the optical indicator may comprise any fixed number of apertures that is at least one less than the total number of apertures. In this case the apertures are selected and arranged so that when rotated, they provide an unambiguous identification of each of the discrete orientations.

Thus, for four apertures, corresponding to four discrete orientations, the indicator may be two adjacent apertures, but not two apertures opposite each other, since two apertures opposite each do not provide an unambiguous identification of each orientation.

FIGS. 7A-7E are schematic views of different orientations of a patient marker 440, according to an embodiment of the present invention. Marker 440 comprises a clamp base 494 which is coupled to an alignment target 444. Clamp base 494 is the base of a clamp 242. Apart from the differences described below, the operation of marker 440, clamp 442, base 494, and target 444 is generally similar to that of marker 40, clamp 42, base 94, and target 44, and elements indicated by the same reference numerals in both markers are generally similar in construction and in operation. Unlike marker 40, where target 44 can only make discrete orientations with respect to clamp 42, target 444 in marker 440 can make multiple non-discrete, substantially continuous, orientations varying from 0°-360° with respect to clamp 442.

FIGS. 7A-7E have been drawn on the same set of xyz axes as for marker 40 (although the axes are rotated 180° compared to those of FIGS. 4B-4E), and orientations are measured as clockwise rotations about the z-axis from the y-axis. FIGS. 7A, 7B, 7C, and 7D, correspond respectively to the target having orientations of 0°, 90°, 180°, and 270° relative to the clamp.

FIG. 7E illustrates the target having an orientation of θ relative to the clamp, where 0°≤θ<360°, and coordinates of a center point of the target region have been marked as (D sin θ, D cos θ) where D is the distance of the target region center point from the z-axis.

In contrast to upper surface 170 of clamp base 94 of clamp 42, an upper xy plane surface 470 of an upper plate 476 of clamp base 494 is circular. Surface 470 has a central circular indent 454 symmetrically situated in the surface, and the indent is terminated at its lower end by a female thread. Surface 470 also has an indent 464 which is in the form of a semicircular arc, centered on a center of circular surface 470. An insert 460 that is a semicircular arc and that is typically colored or retroreflective is inserted into indent 464, and the insert is dimensioned so that an upper surface of the insert is level with surface 470.

A socket 424 of target 444 comprises a planar lower surface 490 which is surrounded by a circular wall 496 that is configured to mate with an outer cylindrical surface 474 of plate 476. Extending from surface 490 are a plurality of arcs 498, distributed symmetrically about a socket central hole 456, configured to mate with indent 454. Socket 424 also comprises a semicircular aperture 468, which is congruent to insert 460.

Target 444 is coupled to clamp 442 by fitting socket 424 to plate 476 so that wall 496 mates with surface 474, and so that arcs 498 mate with indent 454. Once so coupled, target 444 may be held fixedly in place in any orientation selected by professional 22, by screwing a screw 472 into the female thread terminating indent 454.

During a procedure processor 26 is able to determine the orientation of the target, as a value between 0° and 360°, by the imaging of insert 460, and the use of the imaged insert as an optical indicator 462 of the orientation. In one embodiment processor 26 determines the orientation by finding the fraction of the insert visible through aperture 468, as well as a location of the visible insert.

In embodiments of the invention, the fraction may comprise a fractional area of the insert, or alternatively or additionally, a fractional linear dimension, such as an arc length, of the insert. In some embodiments the fractional linear dimension may be measured using a Vernier scale.

Thus, FIG. 7A illustrates a maximum of the insert visible through the aperture, corresponding to an orientation of 0°, and FIG. 7C illustrates a minimum of the insert visible through the aperture, corresponding to an orientation of 180°. FIG. 7B, corresponding to an orientation of 90° illustrates half of the insert visible, the visible half being located below the x-axis, and FIG. 7D, corresponding to an orientation of 270°, illustrates half of the insert visible, the visible half being located above the x-axis.

Other methods for determining the orientation of the target from the imaged insert, such as by finding coordinates of the endpoints of the imaged insert as well as coordinates of an intermediate point on the image, will be apparent, and all such methods are assumed to be comprised within the scope of the present invention.

During a procedure, processor 26 determines the orientation of target 444 from imaging optical indicator 462, as described above. The flowchart of FIG. 8 below describes how the processor uses the values of the orientation during the procedure.

Figure 8:
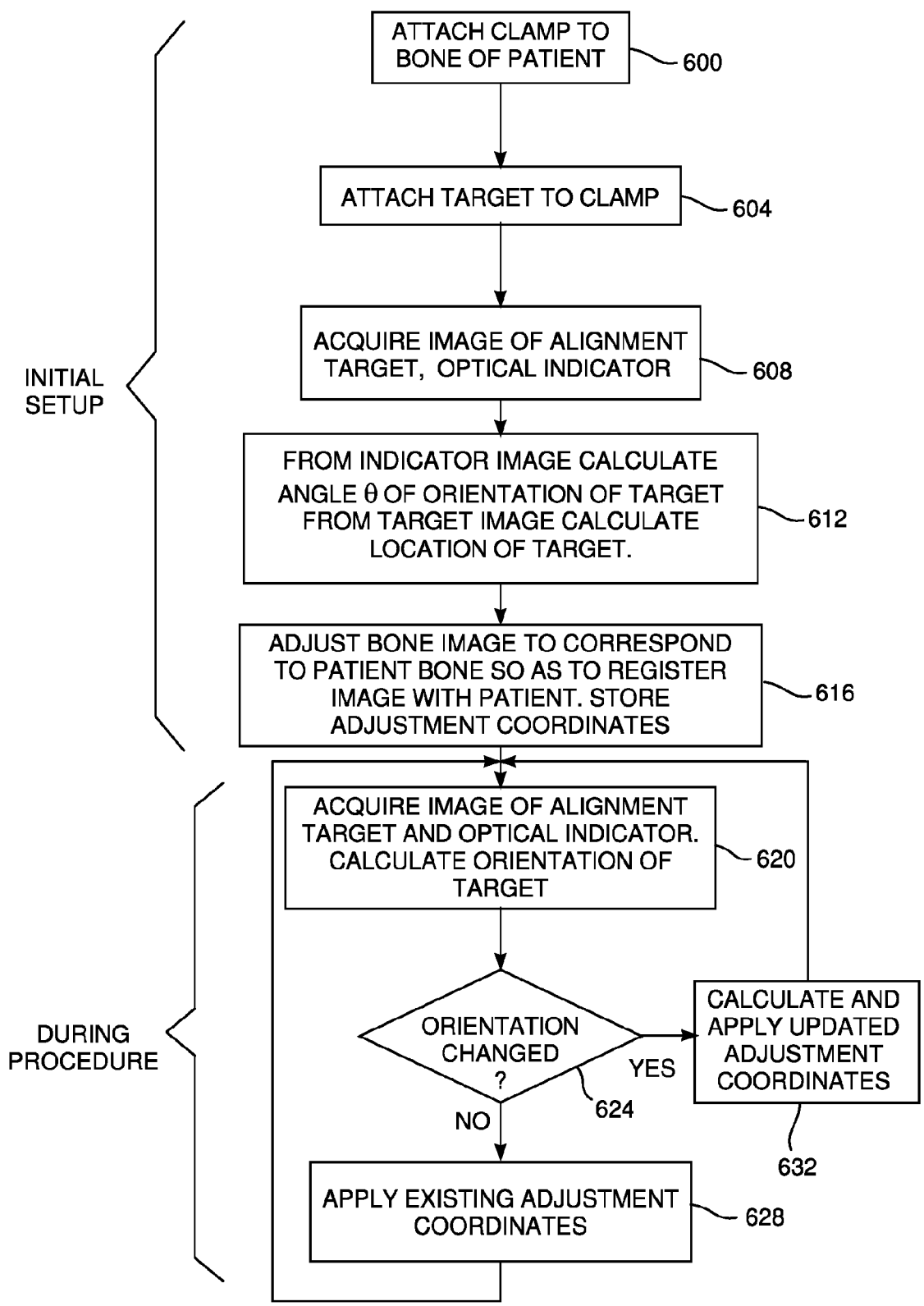
FIG. 8 is a flowchart describing the use of the marker of FIGS. 7A-7E, according to an embodiment of the present invention.
Figure 9:
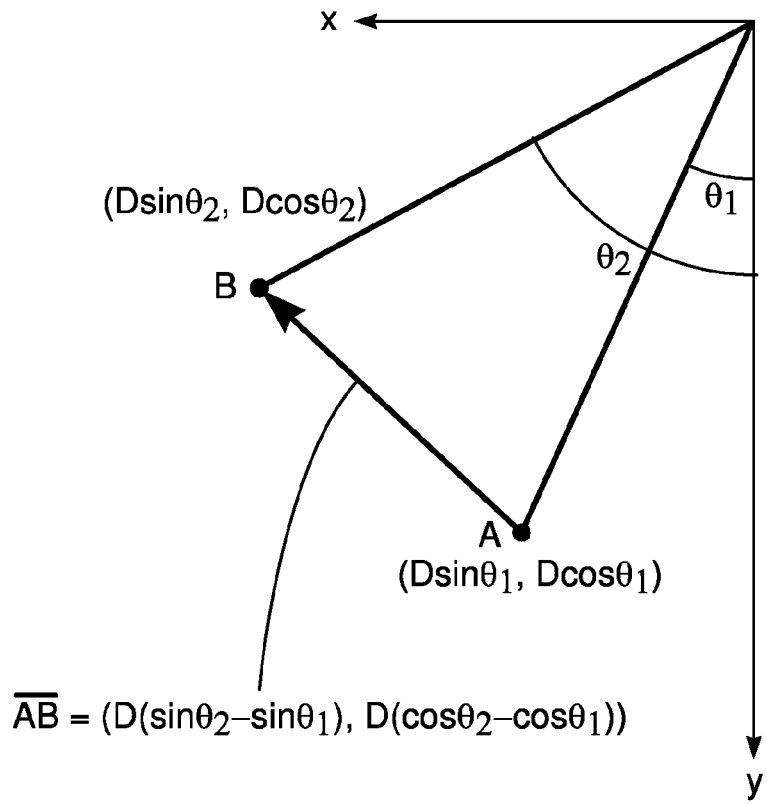
FIG. 9 is a diagram explaining some of the steps of the flowchart of FIG. 8, according to an embodiment of the present invention.

FIG. 8 is a flowchart describing the use of a marker such as marker 440 in the medical procedure referred to above, and FIG. 9 is a diagram explaining some of the steps of the flowchart, according to an embodiment of the present invention.

An initial step 600, wherein clamp 442 is attached to the patient's bone, is substantially similar to initial step 200, described above.

In an attachment step 604, professional 22 attaches socket 424 to base 494, in any convenient orientation of target 444 to clamp 442. The professional uses screw 472 to fix the target to the clamp base.

An imaging step 608 is substantially similar to step 208, described above.

In an analysis step 612, the processor analyzes the image of indicator 462, as described above with reference to FIG. 7E, to determine an angle of orientation θ of the target with clamp 42. In addition, the processor calculates coordinates of the location of target region 120 from the image of the region acquired in step 608.

An adjustment or registration step 616 is substantially as described above for step 216. Thus, in step 616, coordinates of a presented image are adjusted or registered to correspond with an actual image visible to the professional through augmented reality assembly 24. Processor 26 stores the adjustment coordinates, and applies the stored coordinates as an adjustment vector so as to register and track the presented image with patient 30.

Steps 600-616 correspond to an initial setup of navigation system 20 for marker 440. Steps 620-632, described below, correspond to steps of the flowchart that may be implemented during the medical procedure for which system 20 is used.

In a continuing imaging step 620, an image of target 444, including target region 120 and indicator 462 is acquired, e.g., once in a predefined time interval. Optionally, an image of patient 30 may be also acquired. From the image of indicator 462, the processor calculates an angle θ of the orientation of target region 120 relative to the clamp.

In a decision step 624 the processor checks if the angle calculated in step 620 is different from that calculated in step 612, so as to check if the target region has changed orientation. If the decision returns negative, i.e., there is no change in orientation, then in a continuation step 628 the processor continues to use the existing adjustment coordinates, i.e., those of step 616, as an adjustment vector.

If decision 624 returns positive, i.e., there is a change of orientation, then in an update step 632 the processor calculates a change-of-orientation vector, to be added to the existing adjustment vector, so as to enable the processor to maintain registration of images of patient 30 with the patient.

FIG. 9 is a schematic diagram illustrating how the processor calculates the change-of-orientation vector, according to an embodiment of the present invention. A line segment PA, having a length D, represents an initial orientation of adjustment target 444, where A is the center of region 120 and $\theta_1$ is the orientation of the center, both values being measured in step 612. A has coordinates ($D \sin \theta_1$, $D \cos \theta_1$).

A line segment PB, having a length D, represents a subsequent orientation of adjustment target 444, where B is the center of region 120 and $\theta_2$ is the orientation of the center, both values being measured in step 620. B has coordinates ($D \sin \theta_2$, $D \cos \theta_2$).

Processor 26 calculates a change-of-orientation vector [AB] as the difference between the coordinates of B and the coordinates of A, as in equation (1):

$$[AB] = (D(\sin \theta_2 - \sin \theta_1), D(\cos \theta_2 - \cos \theta_1)) \quad (1)$$

Returning to the flowchart of FIG. 8, in step 632 the processor adds a change-of-orientation vector, calculated as described for equation (1), to the existing adjustment vector.

From steps 628 and 632 control returns to imaging step 620 and following that decision step 624, so that during the procedure the processor applies steps 620-632 iteratively.

A positive return of decision 624 is typically caused by professional 22 changing the orientation of target 444 by loosening then tightening screw 472. In some embodiments the professional may pause the tracking of target 444 while positioning the target in a new orientation. It will be understood that there is no need to repeat steps 600-616 after any re-orientation, since by iterating steps 620-632 the processor continues to correctly register any acquired image of patient 30 with the patient.

According to some aspects, a patient marker comprising an alignment target and a marker base, which may be anchored to the patient via an anchoring device, is herein disclosed. The alignment target is coupled to the marker base. The alignment target is configured to rotate around an axis of the marker base. The alignment target comprises an optical indicator, The optical indicator indicates the angle of orientation of the alignment target about the marker base axis. The patient marker further comprises an anchoring interface. The anchoring interface is coupled to the marker base. According to some aspects, the marker base comprises the anchoring interface. The alignment target may comprise a socket configured to fit rotatably to the target base. The patient marker is configured to be mounted on a patient anchoring device, e.g., on a base of the anchoring device, via the anchoring interface in a fixed manner and such that the marker base axis is aligned with the anchoring device base axis (e.g., a clamp base axis). The optical indicator may be, for example, in the form of and may be configured to operate according to optical indicators 162, 262 or 462, as described in and with respect to FIGS. 4A-4E, 6A-6D and 7A-7E correspondingly. The alignment target may be configured to rotate around an axis of the marker base, for example according to the rotation mechanisms describe in and with respect to FIGS. 4A-4E. 6A-6D and 7A-7E. Persons skilled in the art will understand how to implement different mechanisms for the optical indicator and different rotation mechanisms for the alignment target, including those disclosed herein, in a patient marker comprising a rotatable alignment target coupled to a base of the marker. The description above explains how, for example, an optical indicator such as indicator 162, together with the optical elements 138 of alignment target 44, may be used to find an angle of orientation of the alignment target about an axis of a base to which the alignment target is connected. The base may be a marker base or an anchoring device base, such as a clamp base. It will be understood that optical elements 138 identify the alignment target.

In some embodiments of the present invention, professional 22 uses a surgical tool in the medical procedure referred to above (FIG. 1). The tool has a tool marker connected to the tool or integrated with the tool in a predefined location, and the augmented reality assembly (e.g., augmented reality assembly 24) is configured to enable the tracking (e.g., by processor 26) of the position of the tool tip. In these embodiments, instead of using an optical indicator such as optical indicator 162 to identify the angle of orientation of the alignment target, professional 22 may use the tool to find the angle, as is described below.

The patient anchoring device or the marker base may comprise a fixed tool point (also will be referred as "tool point" herein below). The tool point location is configured to be fixed with respect to the anchoring device and thus with respect to the patient. For example, the fixed tool point may be connected to a base of the anchoring device. In general, the tool having the tool marker mounted thereon is calibrated prior to its use in a medical procedure via the augmented reality assembly. In the calibration process, a spatial ratio is determined between the tool marker and the tip of the tool, such as a vector between the tool marker (e.g., a retroreflective predefined point on the tool marker) and the tool tip. The professional may touch the fixed tool point with the tip of the calibrated tool, while the alignment target of the patient marker is oriented in a specific orientation with respect to the anchoring device. An image of the tool marker and the oriented patient marker is captured by the capturing device of the augmented reality assembly. A location of the fixed tool point with respect to the alignment target is determined by a processor, such as processor 26, based on the image. Following that, the orientation of the alignment target with respect to the anchoring device and thus the patient may be determined. According to some aspects, the professional may be directed by the augmented reality assembly (e.g., by a software executed by processor 26) to touch the fixed tool point with the tip of the tool. According to some aspects, the alignment target has a plurality of predefined orientation and a vector between the alignment target and the fixed tool point in each orientation is calculated in advance. In such a case, a spatial area corresponding to each predefined orientation of the target alignment may be determined and used in determining the orientation of the alignment target, e.g., instead of an accurate calculation of the alignment target location. As described above, the capturing device continuously capture images of the area of interest, including the patient marker and the tool marker. For each image captured via the capturing device, the processor may check if the tool tip is substantially located at a possible tool point location, corresponding to a possible alignment target orientation, to identify the touching of the tool point by the tool tip. Identification of a specific such location in one or more subsequent images may determine the orientation of the alignment marker.

Those having ordinary skill in the art will be able to adapt the description, mutatis mutandis, for various configurations of alignment targets, including targets 44, 244 and 444.

It will also be understood embodiments of the invention may measure discrete changes of orientation e.g., of 0°, 90°, 180°, or 270°, or continuous changes of orientation through substantially any angle between 0° and 360°.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:
1. A marker for image guided surgery, comprising:
   a base, having a base axis, connecting to an anchoring device; and
   an alignment target, comprising:
      a target region having an alignment pattern formed thereon;
      a socket connected to the target region and configured to fit rotatably to the base, whereby the alignment target is rotatable about the base axis; and
      an optical indicator for the socket indicating an angle of orientation of the alignment target about the base axis.

2. The marker according to claim 1, wherein the socket is configured to only fit to the base in a plurality of at least two discrete orientations about the base axis.

3. The marker according to claim 2, wherein the plurality of discrete configurations is distributed symmetrically about the base axis.

4. The marker according to claim 2, wherein the plurality comprises four discrete orientations.

5. The marker according to claim 2, wherein the socket comprises a plurality of apertures equal to the plurality of discrete orientations, and wherein the optical indicator is configured to be visible through one of the apertures indicative of one of the discrete orientations.

6. The marker according to claim 2, wherein the socket comprises a plurality of apertures equal to the plurality of discrete orientations, and wherein the optical indicator is configured to be visible through apertures selected and arranged so as to provide an unambiguous identification of each of the discrete orientations.

7. The marker according to claim 1, wherein the socket is configured to fit to the base in a plurality of non-discrete orientations about the base axis.

8. The marker according to claim 7, wherein the socket comprises an aperture, and wherein the optical indicator is congruent with the aperture, and wherein a fraction of the optical indicator visible through the aperture is indicative of one of the non-discrete orientations.

9. The marker according to claim 8, wherein the aperture comprises a semicircular arc.

10. An augmented reality system operative during surgery on a patient, comprising:
    the marker according to claim 1, wherein the socket is at a fixed distance from the target region; and
    a processor configured to: track the alignment target during the surgery, provide a patient tracking vector in response to the tracking of the alignment target, calculate a change in the angle of orientation of the alignment target in response to changes in images of the optical indicator, and add a change-of-orientation vector, based only on the fixed distance and the change in the angle of orientation, to the patient tracking vector so as to update the patient tracking vector.

11. The marker according to claim 1, the marker further comprising the anchoring device.

12. The marker according to claim 1, wherein the anchoring device is a clamp or a pin.

13. A marker for image guided surgery, comprising:
a base, having a base axis;
an interface configured to be coupled to an anchoring device; and
an alignment target, comprising:
   a target region having an alignment pattern formed thereon;
   a socket connected to the target region and configured to fit rotatably to the base, whereby the alignment target is rotatable about the base axis; and
   an optical indicator for the socket indicating an angle of orientation of the alignment target about the base axis.

14. The marker of claim 13, wherein the base comprises the interface.

15. The marker of claim 13, wherein the interface is coupled to the anchoring device in a manner that aligns the base axis with a base axis of the anchoring device.

16. A method for enabling rotation of a marker during surgery without requiring re registration, comprising:
   connecting a base, having a base axis, to an anchoring device;
   forming an alignment pattern on a target region of an alignment target;
   connecting a socket to the target region, the socket being at a fixed distance from the target region and being configured to fit rotatably to the base, whereby the alignment target is rotatable about the base axis;
   providing an optical indicator for the socket indicating an angle of orientation of the alignment target about the base axis;
   operating an augmented reality system during the surgery on a patient; tracking the alignment target during the surgery;
   providing a patient tracking vector to the augmented reality system in response to the tracking of the alignment target;
   calculating a change in the angle of orientation of the alignment target in response to changes in images of the optical indicator; and
   adding a change-of-orientation vector, based only on the fixed distance and the change in the angle of orientation, to the patient tracking vector so as to update the patient tracking vector.

17. The method according to claim 16, wherein the socket is configured to only fit to the base in a plurality of at least two discrete orientations about the base axis.

18. The method according to claim 17, wherein the socket comprises a plurality of apertures equal to the plurality of discrete orientations, and wherein the optical indicator is configured to be visible through one of the apertures indicative of one of the discrete orientations.

19. The method according to claim 17, wherein the socket comprises a plurality of apertures equal to the plurality of discrete orientations, and wherein the optical indicator is configured to be visible through apertures selected and arranged so as to provide an unambiguous identification of each of the discrete orientations.

20. The method according to claim 16, wherein the socket is configured to fit to the base in a plurality of non-discrete orientations about the base axis.

21. The method according to claim 20, wherein the socket comprises an aperture, and wherein the optical indicator is congruent with the aperture, and wherein a fraction of the optical indicator visible through the aperture is indicative of one of the non discrete orientations.

22. A computer-implemented method for enabling rotation of a marker during surgery without requiring re-registration, wherein the marker is anchored to a patient and configured to fit rotatably to a base, and wherein the marker comprises an alignment pattern and an optical indicator, the optical indicator configured to indicate an angle of orientation of the marker about a base axis of the base and the optical indicator is being at a fixed distance from the alignment pattern, the method comprising:
   operating a navigation system during the surgery on the patient;
   tracking the alignment pattern during the surgery;
   providing a patient tracking vector to the navigation system in response to the tracking of the alignment pattern;
   calculating a change in the angle of orientation of the alignment pattern in response to changes in images of the optical indicator; and
   adding a change-of-orientation vector, based only on the fixed distance and the change in the angle of orientation, to the patient tracking vector so as to update the patient tracking vector.

* * * * *